United States Patent
Miller et al.

(12) 
(10) Patent No.: US 6,509,031 B1
(45) Date of Patent: Jan. 21, 2003

(54) SYSTEM FOR POLYMERIZING COLLAGEN AND COLLAGEN COMPOSITES IN SITU FOR A TISSUE COMPATIBLE WOUND SEALANT, DELIVERY VEHICLE, BINDING AGENT AND/OR CHEMICALLY MODIFIABLE MATRIX

(75) Inventors: Douglas R. Miller, College Station, TX (US); Ian R. Tizard, College Station, TX (US); Jimmy T. Keeton, College Station, TX (US); Jerry F. Prochaska, Cordova, TN (US)

(73) Assignee: Board of Regents, Texas A&M University System, College Station, TX (US)

(*) Notice: Subject to any disclaimer, the term of this patent is extended or adjusted under 35 U.S.C. 154(b) by 42 days.

(21) Appl. No.: 09/713,270

(22) Filed: Nov. 15, 2000

Related U.S. Application Data

(60) Provisional application No. 60/165,567, filed on Nov. 15, 1999, and provisional application No. 60/166,024, filed on Nov. 17, 1999.

(51) Int. Cl.[7] ............... A61F 13/00; A61K 9/70
(52) U.S. Cl. .......... 424/443; 424/400; 424/402; 424/422; 424/423; 424/444; 424/445; 424/449; 424/486; 514/781; 514/772.4; 514/772.6; 514/777
(58) Field of Search ................. 424/400, 402, 424/422, 423, 443, 444, 445

(56) References Cited

U.S. PATENT DOCUMENTS 5,376,375 A * 12/1994 Rhee et al. ............... 424/423

* cited by examiner

*Primary Examiner*—Thurman K. Page
*Assistant Examiner*—Charesse Evans
(74) *Attorney, Agent, or Firm*—Fulbright & Jaworski, L.L.P.

(57) ABSTRACT

This invention relates to materials and methods for crosslinking, in situ, proteins, including collagen, with peroxidase, including horseradish peroxidase, to from biocompatible semi-solid gels useful in a number of biological and food product applications.

30 Claims, 19 Drawing Sheets

SYSTEM FOR POLYMERIZING COLLAGEN AND COLLAGEN COMPOSITES IN SITU FOR A TISSUE COMPATIBLE WOUND SEALANT, DELIVERY VEHICLE, BINDING AGENT AND/OR CHEMICALLY MODIFIABLE MATRIX

This application claims priority to U.S. Provisional Application Ser. No. 60/165,567, filed Nov. 15, 1999, which is incorporated by reference herein in its entirety, and claims priority to U.S. Provisional Application Ser. No. 60/166,024, filed Nov. 17, 1999, which is incorporated by reference herein in its entirety.

FIELD OF THE INVENTION

This invention relates to methods of crosslinking proteins, such as collagen, using peroxidase enzymes, such as horseradish peroxidase, in situ, to form biocompatible crosslinked semi-solid gels useful in a number of in vivo and in vitro applications, from wound healing, to drug delivery, to food processing.

BACKGROUND OF THE INVENTION

Various collagen powders, sponges or other artificial constructs including "artificial tissue" or organs for medical uses have been described in the literature and in patents. All of these materials have been prepared ex situ, crosslinked or not, for later application to wounds. The same may be said for the use of collagen for augmentation of processed foods (meats, poultry). The inventors are not aware of any currently available products using collagen, or collagen used in combination with other co-reactants or additives, that can be prepared as a solution and applied by injection or pouring of a liquid at the site of interest (wound tissue or chopped meat or poultry), where covalent polymerization and bonding to the site is accomplished in situ. The closest known such wound sealants are polymers of purified fibrinogen (Sierra, 1993), crosslinked by addition of thrombin, and cyanoacrylate cements. The former represent the natural plasma proteins, in purified form, involved in clot formation. For human use they must be prepared from human plasma due to immunological considerations, and are used primarily in Europe and Asia (e.g., Japan), but have not been approved by the FDA (as of 1996) for U.S. use. Cyanoacrylate cements are more commonly known, for household use, as 'superglue'. Both the fibrin and cyanoacrylate wound sealants are used primarily as alternatives to sutures (i.e., to seal surgical wounds), and have the disadvantage of forming such a dense polymer as to be only slowly biodegradable, thus often retarding wound remodeling and repair (Lasa et al., 1993). Neither is suitable for filling of larger wound beds or for use as a delivery vehicle for other components. Minor soft tissue wounds normally are capable of good repair with minimal treatment. More serious injuries (e.g., trauma), recalcitrant wounds (e.g., decubitus ulcers) or tissue repair which is compromised by other factors (e.g., age, diabetes) require assistance to heal. Healing of such wounds often is further complicated by infection, and where repair is finally achieved it occurs via scarring and contracture, usually resulting in some loss of cosmetic appearance and/or function. Attempts to improve repair may be made by mechanical means, where wound strength and barrier function are aided by a bioinert material (e.g., bandage) or by a biologic approach (e.g., resorbable sponges, grafts, "artificial skin") which encourages regenerative repair. The former materials eventually must be removed, while materials for the latter often are deficient in mechanical strength, elasticity, or availability, are immunogenic or cytotoxic, or are expensive.

A similar adhesive for food use is Fibrimex®, distributed in North America by F.N.A. Foods, Inc. It also is based on fibrinogen-thrombin reaction (materials obtained from bovine plasma) and will react at low temperature (4° C.), but must be mixed very quickly with the meat products being reformed since the reaction proceeds to completion in less than 30 minutes.

SUMMARY OF THE INVENTION

We have demonstrated the feasibility of a new collagen-based wound sealant which can be gently but covalently crosslinked to a wound bed via a catalyzed chemical reaction utilizing peroxidase enzyme (primarily, horseradish peroxidase) and hydrogen peroxide ($H_2O_2$). Unlike other collagen compositions that are prepared ex situ, this material is prepared as a thick liquid that is poured or injected into the site of interest immediately upon activation by the catalyst, whereupon it polymerizes in situ. Good mechanical strength and elasticity by the polymer is achieved, cellular compatibility and faster healing is demonstrated, and the sealant can be prepared at relatively low cost. In addition, the base material could be modified by inclusion of other matrix components, co-reactants, non-reactive materials, growth factors, antibiotics and microbeads (e.g., of potential use for delayed-release of additional components). This material is particularly useful for emergency wound repair (e.g., use 'in the field'), for repair of recalcitrant wounds (e.g., decubitus or pressure ulcers), and long-term regenerative type repair of a wound. Additional uses for this material include a slow release depot for vaccines, adjuvants or drugs, bone repair, graft or prosthetic implant stabilization, and as a binding agent for restructured foods (e.g., sausages, 'poultry rolls', restructured meats). This material thus represents a new product and composition of matter as well as a potential improvement of existing products and compositions currently available.

This material has use throughout veterinary medical, human medical and dental practice, and the food industry.

Collagen may be crosslinked by a variety of chemical or physical means (for reviews, see Rault et al., 1996; Jain, 1992; Meade and Silver, 1990) and the products subsequently used (crosslinked or not) in various wound repair materials (Pachence, 1996; Choucair and Phillips, 1996; Jeter and Tintle, 1991). While these products may have acceptable mechanical strength, antigenicity and permeability to cellular ingrowth and remodeling, none of the crosslinking methods are compatible with living cells and therefore cannot be employed in situ. Crosslinking of collagen solutions into gels using lactoperoxidase (Tenovuo and Paunio, 1979) or horseradish peroxidase (LaBella et al., 1968) has been demonstrated and the formation of small amounts of dityrosine reported, however, no use for these collagen gels was demonstrated or suggested.

We have explored the use of peroxide-peroxidase catalyzed crosslinking of collagen with the aim of developing one or more compositions or materials that may be used by the medical, pharmaceutical or food industries. The following are embodiments of the present invention.

One embodiment relates to a method of covalent crosslinking of acid-soluble Type I collagen from calf skin with horseradish peroxidase (HRP)-hydrogen peroxide ($H_2O_2$, $O_2$, Px) (collagen polymer). Collagen solutions of 8–12 mg/ml can optimally be crosslinked into a semi-solid gel by addition of HRP and peroxide in molar ratios of 4–5:1:50 to 4–5:1:200 collagen:HRP:peroxide (molecular weight basis, e.g., moles of each component). Controls lacking either HRP or peroxide failed to form a gel. Greater ratios of collagen relative to HRP (e.g., 20:1:200) or substantially higher concentrations of peroxide (>400 parts) did not provide optimal polymerization.

That a crosslinked polymer was being formed was confirmed by decreased solubility of the matrices in hot (75° C.) sodium dodecyl sulfate (SDS) solution, and an increase in high molecular weight components observed by SDS agarose gel filtration and SDS-polyacrylamide gel electrophoresis with a concomitant decrease in lower molecular weight components (monomers).

The matrix was found to have significant mechanical strength and elasticity by Instron compression analysis and deformation testing, and was superior in these respects to glutaraldehyde crosslinked positive control preparations. Uncrosslinked materials had no demonstrable mechanical strength as measured by either method.

Other embodiments relate to the crosslinking of interstitial collagen types II, III and of type IV collagen (basement membrane type) in the presence of HRP: peroxide, therefore the method is useful for both interstitial and basement membrane collagens.

One embodiment relates to the solidification (crosslinking) of solutions of type I collagen using soybean peroxidase (Sigma®) and microbial peroxidase (Sigma®, from *Arthromyces ramosus*), although to a lesser apparent degree than with HRP. The method thus appears to be generally applicable to the use of any peroxidase.

Other embodiments cover the fact that other proteins (i.e., fibrinogen, recombinant fibronectin-like engineered protein polymer, Sigma®), alone or in combination with type I collagen, can be crosslinked in this system.

Another embodiment relates to a co-polymer of type I collagen and fibrinogen, resulting in greater mechanical strength than an equal amount of collagen alone.

Another embodiment relates to the fact that some proteins (e.g., bovine serum albumin, BSA) apparently are not crosslinked in the peroxide:peroxidase system. This protein could, however, be incorporated into collagen gels (1 mg BSA per 10 mg/ml collagen type I, i.e., 10 weight percent relative to collagen) without interfering appreciably with the crosslinking of the collagen. Thus, the matrix can be useful as a depot for the delivery of materials which do not participate in or are altered by the action of HRP:peroxide (e.g., for vaccines, adjuvants, growth factors, drugs).

Another embodiment relates to microbeads, using Sephadex G25, fine beads as a model system, can be incorporated into the collagen polymer matrix by at least 10 weight percent with no apparent effect on the mechanical strength or integrity of the matrix. Thus, materials incorporated into (biodegradable) microbeads may potentially be incorporated into the matrix for timed (delayed) release of entrapped components (e.g., vaccines, adjuvants, growth factors, drugs).

Further, in another embodiment, the polymer is useful as a three dimensional matrix for the growth of dermal fibroblasts (e.g., mouse 3T3 cells) in vitro. Cells readily grow into, proliferate in and remodel the matrix without signs of any cytotoxicity.

A still further embodiment relates to the fact that the collagen matrix can be modified by the addition of recombinant fibronectin polymer (Fn) and/or human placental hyaluronic acid (HA)(Sigma®). An optimal addition of 0.5% Fn and 1% HA was found in vitro to significantly encourage cell ingrowth, proliferation and protein synthesis as determined by labeling of 3T3 cells with $^3$H-thymidine and $^{14}$C-proline, over a period of one week. Histological observations confirmed the radioisotopic incorporation results.

In another embodiment, recombinant human basic fibroblast growth factor (rhbFGF) can be added to the collagen matrix prior to polymerization, or to the matrix plus Fn/HA, and will produce increased cellular proliferation and protein synthesis above that seen with the base collagen matrix or Fn/HA modified matrix alone (control matrices) over a period of one week. Thus, growth factors/cytokines may be added to the matrix and retain effective cell stimulating activity above and beyond that of the matrix polymer components alone.

Still further, repeated in vivo applications of the polymer in rats and mice indicate that the collagen polymer is weakly or non-immunogenic. Subcutaneous injection of the polymer in mice persists for at least 5 days to 2 weeks, further indicating its potential for use as a delivery depot. No inflammatory reaction, upon histological examination, was found after four exposures to the polymer over an eight week period indicating that the material is safe for repeated exposure.

Furthermore, in another embodiment it has been shown that the collagen polymer improves healing of granulation-type wounds in rats by, at minimum, decreasing initial wound expansion. Decreased scar formation also may result, although this was not quantified.

Still further, it has been shown that Fn/HA modified matrix significantly improves healing of granulation-type wounds in rats, and that addition of rhbFGF to the modified matrix results in even greater improvement of healing by, at minimum, decreasing initial wound expansion. Decreased scar formation also may result.

Additionally, in another embodiment, it has been demonstrated that the matrix has an inhibitory effect on the growth of Staphylococcus aureus in agar plate culture when the peroxide was included in the mixture. Further inhibition of bacterial growth was achieved by inclusion of a "model" antibiotic (gentamicin) in the polymer. Polymer formation was inhibited by direct inclusion of the antibiotic into the collagen matrix, suggesting co-reaction which resulted in interference with the crosslinking reaction of the collagen. It is suggested that antibiotics or other appropriate drugs or other bioactive compounds can be incorporated into biodegradable microbeads for delayed release, and that these beads can be incorporated into the collagen matrix essentially as stated above. This delivery system would be a more effective means of inclusion of such materials into the collagen-based matrix as a method of avoiding participation in the crosslinking reaction initiated by peroxide:peroxidase.

It has further been demonstrated that in embodiments where dilute solutions of type I collagen are reacted with a molar excess of either phosposerine or phosphoarginine in the presence of HRP-peroxide, the apparent molecular weight of the $\alpha_1$, and $\alpha_2$ chains, after separation by SDS-PAGE, increases slightly. The increase suggests a covalent binding of the phospho-amino acids in ratios of about 2.5–3.5 residues per collagen chain. It is suggested that the collagen chains thus can be directly modified by addition of other components via HRP-peroxide catalyzed reaction.

Still further it has been demonstrated that in some embodiments the collagen polymer may be mixed with or applied to the surface of meat and poultry tissues for use as a food binding/restructuring agent. The liquid nature of the starting material allows thorough blending with the minced or chopped meat or poultry via mechanical mixing, and will polymerize over a period of hours at 4° C. The restructured products maintain a superior degree of cohesiveness and tenderness after cooking to USDA approved endpoint temperatures. All components of the polymer are food grade and acceptable for incorporation into meat products. The antimicrobial activity of the reactants described above may have food safety implications for the food industry. The addition of other materials (e.g., alkaline phosphates, sodium chloride) to the collagen polymer also can augment its structural/biomechanical properties in this application.

An embodiment of the invention, the collagen polymer, with or without additional additives or the addition of phospo-amino acids, also may provide a matrix material suitable for stimulation of mineralization and which might be useful for bone repair and for fixation of orthopedic (e.g., hip replacements) or dental implants in bone.

An embodiment of the invention, the collagen polymer, with or without additional additives, also may be useful for graft augmentation (e.g., skin grafts), to augment healing of surgical injuries, or for cosmetic injection procedures.

The use of peroxide with peroxidase (primarily HRP) to gel and apparently crosslink and polymerize collagen (primarily acid soluble type I) has been demonstrated. Assessments of mechanical strength and elasticity have been made and compared to appropriate positive and negative controls. The ability to add other components to the collagen matrix has been demonstrated. The ability of skin fibroblasts to grow in vitro into the matrix with significant proliferation and synthetic activities has been shown. Formation of the collagen polymer in vivo in granulating wounds or subcutaneous injections in rats and mice, with subsequent persistence at the application site, has been demonstrated. A lack of inflammatory reaction to the collagen matrix, combined with its in vivo resorption and apparent ability to facilitate wound closure, was observed. The ability of the catalyzed collagen matrix to bind meat particles together in a useful fashion for restructuring of meat/poultry products has been demonstrated.

Non-limiting examples of advantages of the present invention include, but are not limited to, the following:

The material is easily and cheaply prepared for medical use, relative to current wound repair materials.

It is readily shaped to fit where needed since it is applied as a liquid.

It is tissue-compatible for covalent crosslinking in situ, thus binding to the wound bed as well as to itself.

It uses no toxic chemicals at any point in its preparation, thus is less likely to cause an inflammatory reaction than, e.g., glutaraldehyde crosslinked collagen.

It does not have to be rehydrated, like dry collagen preparations.

It retains a high degree of elasticity along with a reasonable mechanical strength, and thus can stretch within a wound bed without tearing or pulling excessively on the margins of the wound.

The polymer has inherent antimicrobial activity (which can be enhanced by added antibiotics), thus can reduce the incidence and severity of later complications when applied to contaminated wounds.

It is readily invaded by cells and degradable for remodeling and replacement (unlike fibrinogen or cyanoacrylate glues).

The matrix can be readily modified by addition of other components/co-reactants, thus having the potential to be tailored to a particular application.

The material initially is injectable and persists long enough to be useful as a slow release depot, e.g., for vaccines, adjuvants, drugs or other bioactive materials.

The material also will accommodate a reasonable load of microbeads, and thus can deliver materials that are initially protected from the peroxide-peroxidase reaction.

The addition of bioactive components to the collagen matrix, along with additional components contained in biodegradable microbeads, provides a mechanism for the sequential delayed release of two or more components ("time release-time release').

The matrix can be readily mixed with meats and poultry and reacted at low temperature (e.g., 4° C.) to contribute strength and cohesiveness to the food product. It also has been shown to withstand cooking temperatures of at least 71° C. while still making significant contributions to the food products.

Where a protein is referred to, in the specification and claims, it is intended that the coverage refers to wild type protein, naturally or recombinantly expressed, as well as to derivatives of the protein, including, but not limited to, deletions, insertions, modifications and the like known in the art.

Other and further objects, features and advantages would be apparent and eventually more readily understood by reading the following specification and by reference to the company drawing forming a part thereof, or any examples of the presently preferred embodiments of the invention are given for the purpose of the disclosure.

Day 4: Base+2 ng, sol, NS; Base+2 ng, mat,P<0.10; Base+5 ng, sol, P<0.02; Base+5 ng, mat, NS. Best+2 ng, sol, NS; Best+2 ng, mat, P<0.05; Best+5 ng, sol, P<0.001; Best+5 ng, mat, P<0.01.

Day 7: Base+2 ng, sol, P<0.05; Base+2 ng, mat, P<0.02; Base+5 ng, sol, P<0.02; Base+5 ng, mat, P<0.01. Best+2 ng, sol, NS; Best+2 ng, mat, P<0.01; Best+5 ng, sol, P<0.05; Best+5 ng, mat, P<0.02.

Figure 13:
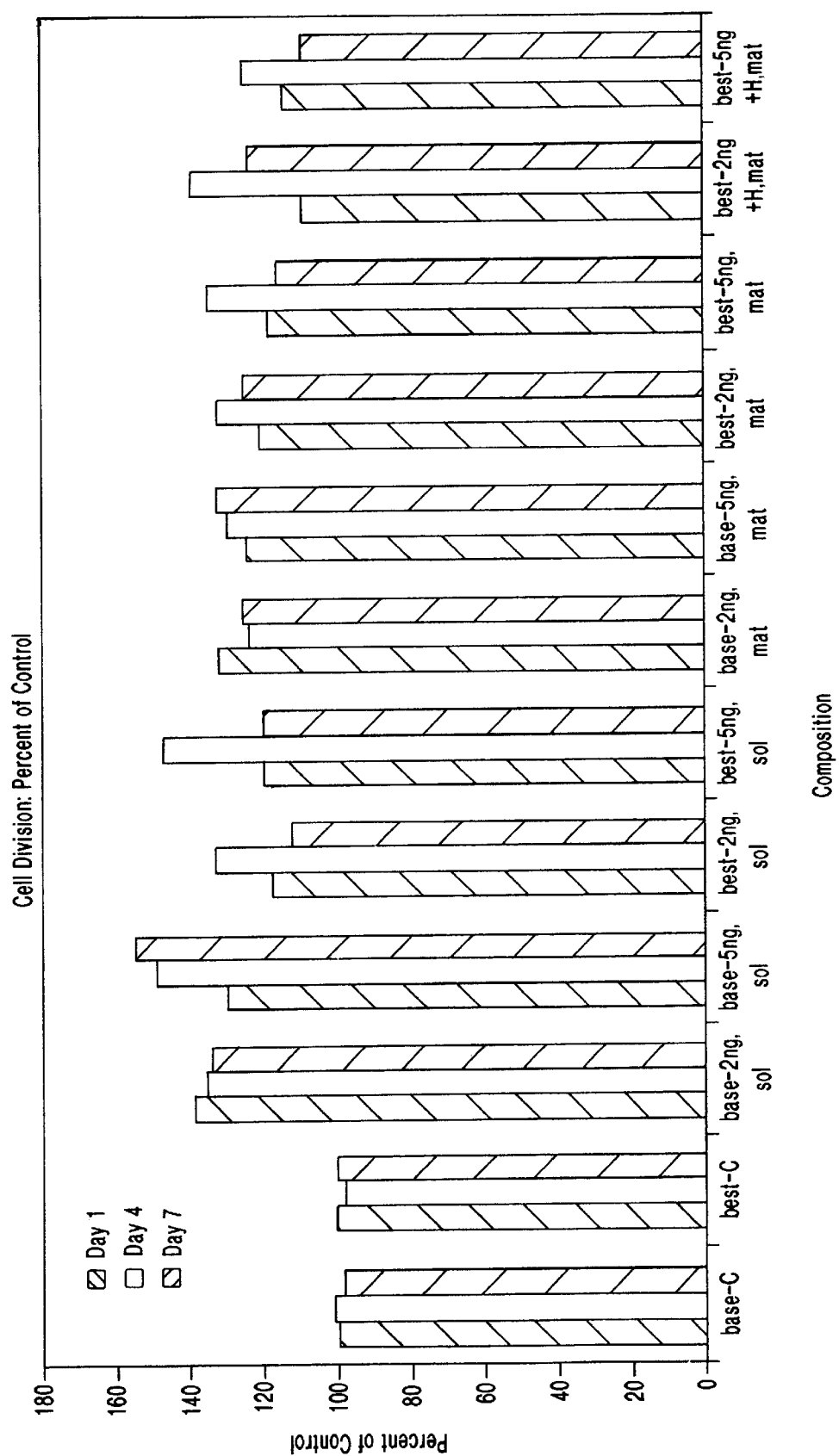

FIG. 13. Effects of recombinant human basic Fibroblast Growth Factor (rhbFGF) on cell division activity ($^3$H-thymidine incorporation) by 3T3 fibroblasts cultured on the collagen- based polymer matrices. Control (collagen alone, 10 mg/ml) matrix levels (base-C) and "best" matrix (collagen, 10 mg/ml+0.5% Fn+1% HA) were taken as 100% and other preparations were expressed, respectively, as a percent of the control values at the times indicated (1, 3, and 7 days after plating). The first 2 samples represent the base and best matrix control values without added rhbFGF; the next 4 samples were incubated with 2 or 5 ng/ml rhbFGF added in solution to the culture medium (sol) to the base and best matrices; the next 4 samples with rhbFGF incorporated directly into the collagen polymer matrices (mat) as described in the text; and the final 2 preparations were the best matrix containing rhbFGF which first was combined with an equimolar amount of heparin (H) before incorporation into the collagen polymer matrix. This made no significant difference. In all of the (mat) preparations, the bFGF was added only once, while cultures receiving it in solution received fresh rhbFGF at each medium change/addition (i.e., for every 1 ng added once in the polymer, a total of 4.25 ng was added over the course of a week to culture aliquots). N=10 replicates. Student's t values (two-tailed test) for the most significant comparisons of experimental preparations versus respective controls were: Day 1: Base+2 ng, sol, $P<0.001$; Base+2 ng, mat, $P<0.001$; Base+5 ng, sol, $P<0.001$; Base+5 ng, mat, $P<0.01$. Best+2 ng, sol, $P<0.01$; Best+2 ng, mat, $P<0.001$; Best+5 ng, sol, $P<0.002$; Best+5 ng, mat, $P<0.002$.

Day 4: Base+2 ng, sol, $P<0.002$; Base+2 ng, mat, $P<0.05$; Base+5 ng, sol, $P<0.01$; Base+5 ng, mat, $P<0.02$. Best+2 ng, sol, $P<0.001$; Best+2 ng, mat, $P<0.001$; Best+5 ng, $P<0.001$; Best+5 ng, mat, $P<0.0005$.

Day 7: Base+2 ng, sol, $P<0.001$; Base+2 ng, mat, $P<0.002$; Base+5 ng, sol, $P<0.001$; Base+5 ng, mat, $P<0.01$. Best+2 ng, sol, NS; Best+2 ng, mat, $P<0.07$; Best+5 ng, sol, NS; Best+5 ng, mat, NS.

Figure 14:
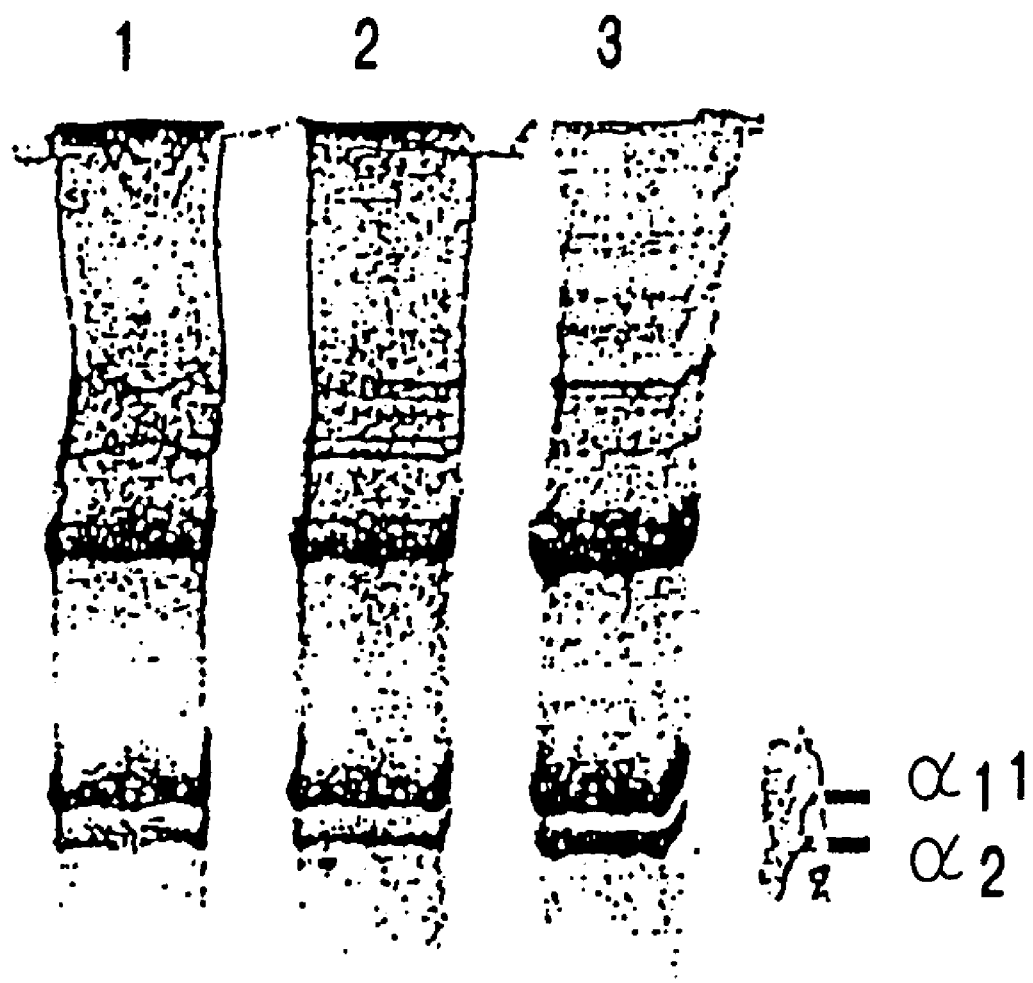

FIG. 14. SDS-polyacrylamide gel electrophoretic separation of type I collagen:, 1) after reaction with a 1500 molar excess of phospho-arginine; 2) after reaction with a 1500 molar excess of phospho-serine, and; 3) unreacted (control) collagen. A small increase in the molecular weights of both the $\alpha_1$ and $\alpha_2$ collagen chains reacted with the phospho-amino acids, corresponding to an estimated binding of 2.5–3.5 residues of the phospho-amino acids per collagen chain, was measured based on molecular weight analyses on a Bio-Rad Fluor-S densitometer as compared to the control collagen.

Figure 15:
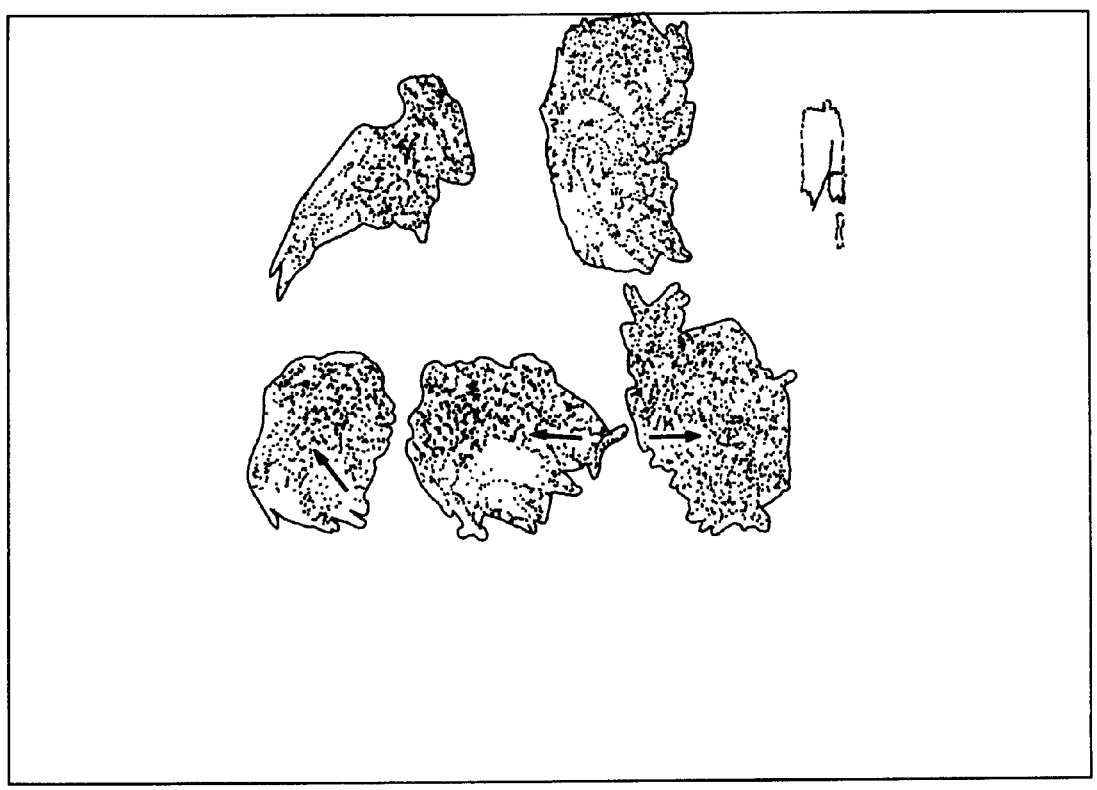

FIG. 15. Post-mortem mouse skin samples taken after four injections of unpolymerized collagen mixture (10 mg/ml type I collagen+0.35 mg/ml HRP, no peroxidase)(top two specimens) or four injections of collagen polymer (10 mg/ml type I collagen+0.35 mg/ml HRP+0.006% peroxide) (bottom three specimens). The specimens were obtained four days after the last injection, which were given at two week intervals. Nodules of the injected collagen polymer can be seen in the bottom three specimens (arrows). No histological evidence of an inflammatory reaction in any of the specimens was found (not shown).

Figures 16A, 16B, 16C:

FIG. 16. Appearance of granulating (punch biopsy) wounds from one of the treated rats. A. 1 day, B. 6 days, and C. 10 days post-wounding. The relative areas (mm$^2$) of treated:control wounds (left:right) are: A. 24.1:27.6, B. 16.6:24.8, and C. <2.0:5.8.

Figure 17:
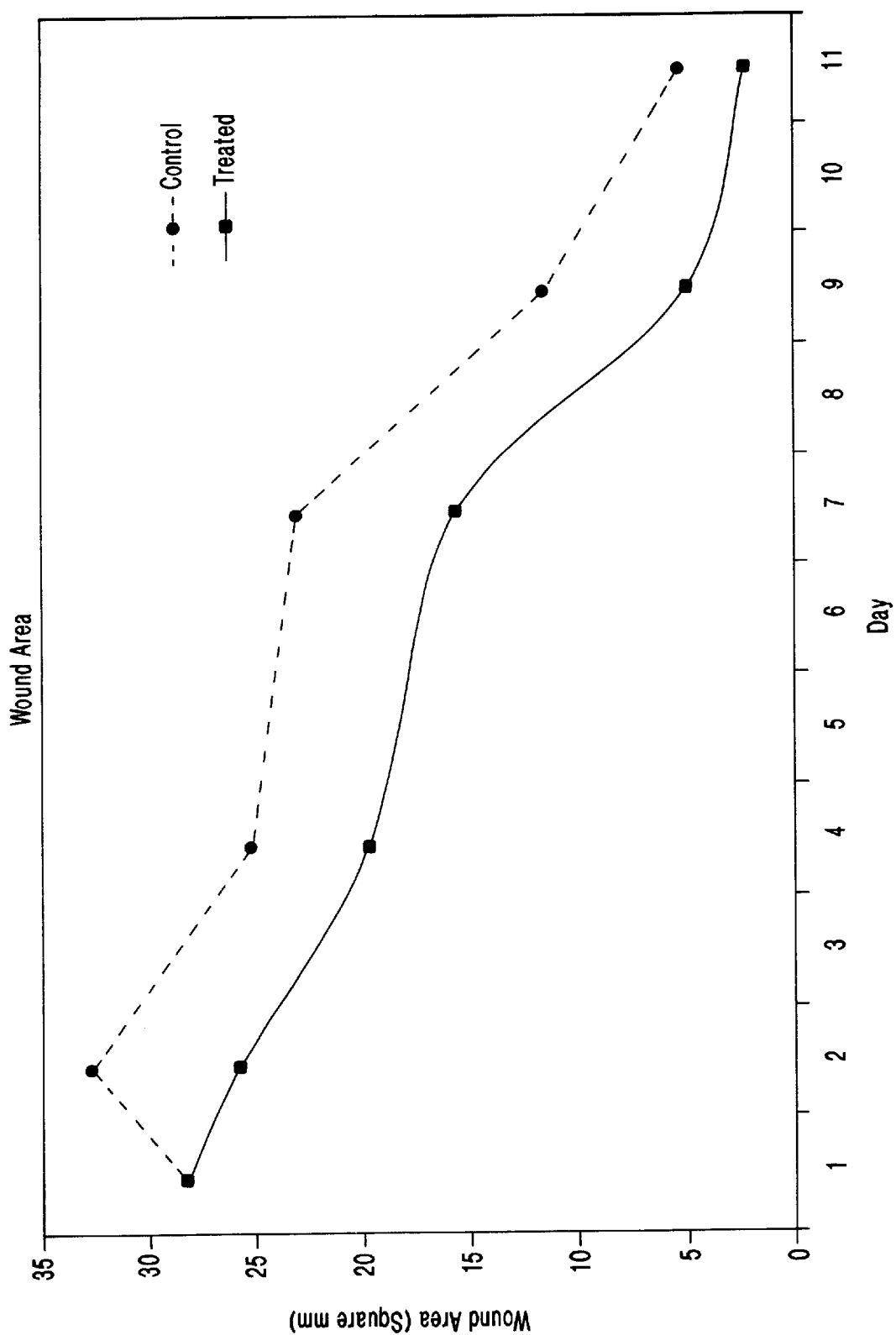

FIG. 17. Healing of 6 mm round punch biopsy wounds (full thickness) in mature (6–8 mo.) rats with time. Upon initiating HRP:Px crosslinking, approximately 0.2 ml of a 10 mg/ml collagen solution was placed into the wounds on the left side and allowed to polymerize in situ. The contralateral wound was filled with uncatalyzed (control) collagen mixture. Wound size was determined by planimetry.

Figure 18:
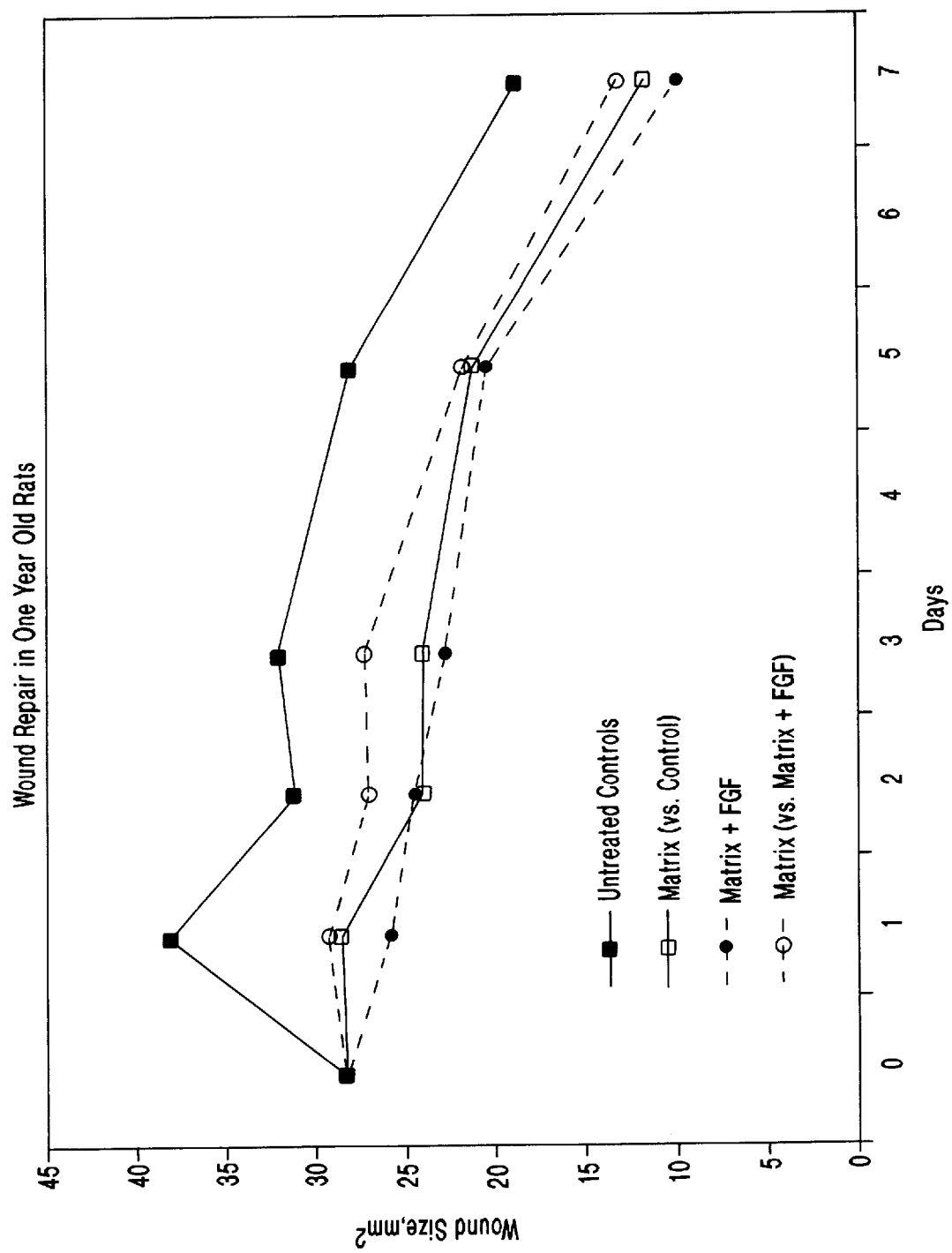

FIG. 18. Healing of 6 mm round punch biopsy wounds (full thickness) in rats with time. These results represent the averages of two wounds in each of four rats (8 wounds total) for each treatment group. Both wounds on one side of an individual were given the same treatment, with equal numbers of rats receiving a given treatment on the left and right sides. Control wounds in 4 rats were given no treatment. The contralateral wounds were filled with the matrix material (10 mg/ml type I collagen+100 μg/ml hyaluronan+50 μg/ml synthetic fibronectin polymer) immediately upon activation of the crosslinking reaction. In the other 4 rats, one pair of wounds was filled with the matrix while the contralateral wounds received the matrix containing in addition 8 ng/ml rhbFGF. Statistical evaluations using a two-tailed Student's t test gave the following:

Control vs. Matrix: Day 1, $P<0.02$; Day 2, $P<0.002$; Day 3, $P<0.002$; day 5, $P<0.005$; day 7, $P<0.025$.

Control vs. Matrix+FGF: Day 1, $P<0.001$; Day 2, $P<0.01$; Day 3, $P<0.0005$; day 5, $P<0.002$; day 7, $P<0.01$ Matrix+FGF vs. Contralateral Matrix: Day 1, NS; Day 2, NS; Day 3, $P<0.05$; day 5, NS; day 7, $P<0.05$.

DETAILED DESCRIPTION OF THE INVENTION

It is readily apparent to one skilled in the art that various embodiments and modifications may be made to the invention disclosed in this Application without departing from the scope and spirit of the invention.

a. Subjective Evaluations and Preparation of Type I Collagen Polymer

It is expected that a number of factors are likely to influence the time course of collagen matrix polymerization, as well as the properties of the final product. These primarily included the stochiometric ratios of collagen: HRP: Px, the pH and salt composition of the reaction medium, the temperature at which the reaction is done and the addition of other (non-collagenous) components. Subjective evaluations of the polymerization (crosslinking) were done in the following manner.

The stochiometric ratio of type I collagen molecules (Sigma®, tissue culture grade, from calf skin, acid soluble, lyophilized) to horseradish peroxidase (Sigma® type XII, affinity purified, salt free, 310 units/mg) to peroxide (Fisher ACS, $H_2O_2$, 30% solution) first was considered. To facilitate comparisons, all ratios were calculated on a molecule per molecule (molar) basis, with components being present in nanomole-micromole quantities. Samples (0.5 ml) were prepared in 1.5 ml microcentrifuge tubes, using gentle vortexing or stirring (i.e., avoiding the formation of air bubbles) to thoroughly mix the components.

The preparations were made as follows. Using a stock solution of 20 mg/ml type I collagen in 0.01 M HCl, final collagen concentrations of 6 to 14 mg/ml were prepared. At each concentration of collagen, the ratio of collagen:HRP was varied from 1:1 to 20:1. Similarly, the ratio of HRP:Px was varied from 1:50 to 1:1000. The collagen solution first was neutralized to pH ~7 with a 0.2M sodium phoshpate buffer, immediately followed by addition of the HRP in phosphate buffer, immediately followed by addition of the Px (working concentration of 0.3%) with stirring after each addition. Solidification of the samples was done at room temperature (~20° C.) or at 37° C. and observed for up to 30 minutes. Negative controls included type I collagen prepared without HRP or Px, while positive controls were polymerized by addition of a freshly prepared neutral glutaraldehyde solution to a final concentration of 0.01%.

As an example: 250 μl of collagen type I (20 mg/ml) was mixed with 140 μl of 0.01M HCl. 0.2M sodium phosphate buffer, pH ~7.0, 90 μl, along with 10 μl of HRP in phosphate buffer containing 0.33 mg of HRP, were added to the above and mixed by gentle vortexing or by stirring with a stirring rod with care being taken to avoid introduction of bubbles into the mixture. Immediately following this mixing, 10 μl of 0.3% $H_2O_2$ in phosphate buffer was added with a micropipettor and gently mixed as above. The final volume produced was 0.5 ml. The mixture was allowed to react for up to 30 minutes at room temperature, or was placed into a 37° C. incubator and allowed to react for up to 30 minutes without further mixing or disturbance. The exact order of addition/mixing of the components did not seem to make any significant difference in the final product formation, however, the mixing had to be done forthwith to avoid precipitation of the collagen solution by neutralization with phosphate buffer before polymerization could occur. Otherwise, the crosslinking reaction would not achieve the desired level of solidification of the collagen gel.

No polymerization (crosslinking, or cohesiveness) of the collagen at any concentration was obtained when: 1) HRP but no Px was present; 2) Px but no HRP was present; 3) HRP was boiled for 30 minutes before addition to the sample; 4) no glutaraldehyde was present. Thus, either active catalyst (HRP) plus co-substrate (Px) or chemical crosslinker (glutaraldehyde) had to be present for solidification of the collagen solution to occur.

Collagen concentrations of 8–12 mg/ml produced what seemed to be the most useful collagen gels. At 6 mg/l, the gels formed were loose, viscous polymers which could not retain the full liquid volume of the mixture, while concentrations above 12 mg/ml had such a high initial viscosity that thorough mixing with the other components was extremely difficult. In general, it was observed that the most rapid initial polymerization was achieved at lower molar ratios of collagen:HRP (i.e., 2:1, 4:1, and at the lowest ratios of HRP:Px (i.e., 1:50, up to 1:400). Higher ratios of the latter usually resulted in no polymerization, or even a decrease in viscosity of the original collagen mixture, possibly due to hydrolysis of the collagen at the elevated Px concentrations. A 1:1 ratio of collagen:HRP resulted in less polymerization than did the 2:1 or 4:1 ratios. The best overall polymerization was observed at the intermediate ratio of collagen:HRP (i.e., 4–5:1) and HRP:Px ratios of 1:100–200. The final degree of polymerization appeared to be achieved (ratio of collagen:HRP:Px=4:1:200) in 15–20 minutes at room temperature, and 5–15 minutes at 37° C. Collagen solutions that were neutralized (pH ~7), but lacking either HRP or Px, formed a loose precipitate ('gel'), but had no structural integrity. By comparison, crosslinking in the presence of 0.01% glutaraldehyde was slow (>1 hour), although the final degree of solidification was comparable to the HRP:Px-catalyzed samples of collagen. In addition, the variation of final reaction pH over the relatively physiological range of 6.5–7.5 produced no obvious difference in the extent of polymerization. Crosslinking of collagen neutralized with a final phosphate buffer concentration of 0.04M versus a phoshpate buffered saline concentration of 0.01M phosphate buffer, 0.15 M NaCl also appeared to be similar, indicating that variations in salt content over a physiological range had no effect on the final product.

Also investigated was the crosslinking of type I collagen by soybean peroxidase (SBP)(Sigma®, 80 units/mg) and peroxidase from *Arthromyces ramosus* (Sigma®, 60 units/mg). Both were found to produce a solid collagen gel, but one with less apparent strength and integrity than those produced by the action of HRP. The lower level of activity/purity of these peroxidases may explain the difference.

b. Physical Properties of Collagen Types I–IV Polymers and Matrix Co-polymers

Collagen samples (Sigma®, type I acid soluble calf skin, human placental types III and IV, bovine nasal septum type II) were polymerized overnight at room temperature, and then were heated at 75° C. for 1 hour in 1 ml/ 0.5 ml collagen preparation in 5% sodium dodecyl sulfate (SDS), 0.01 M phosphate buffer, pH ~7 (strongly denaturing conditions). In addition, bovine fibrinogen (Sigma®, type IV, 95% clottable) was polymerized alone or co-polymerized with the type I collagen at 10 or 20 weight % (i.e., 1 mg. fibrinogen+9 mg collagen or 2 fibrinogen+8 mg collagen in a 10 mg/ml final concentration of polymer matrix).Bovine serum albumin (Sigma®) also was tested. Samples were centrifuged to pellet insoluble material, the supernatants were removed and the pellets lyophilized and weighed to determine percent solubilization.

Figure 1:
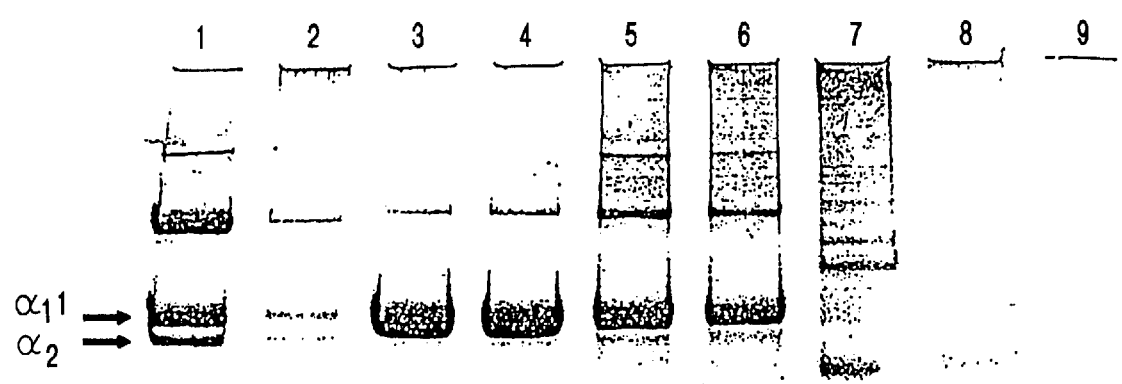
FIG. 1. SDS-polyacrylamide gel electrophoretic separations of collagens. 1) Type I, before reaction with HRP-Px, 2) after crosslinking by HRP-Px; 3) type II collagen before reaction, 4) after crosslinking; 5) type III collagen before reaction, 6) after crosslinking; 7) type IV collagen before reaction, 8) after crosslinking; 9) glutaraldehyde crosslinked collagen type I. Identical loadings of 15 µg/lane of starting material (based on samples before crosslinking and solubilization of the starting material, 10 mg/ml collagen) was used for all samples. The arrow indicates the $\alpha_1$, (I, II, and III) region of the collagen monomer.
Figure 2:
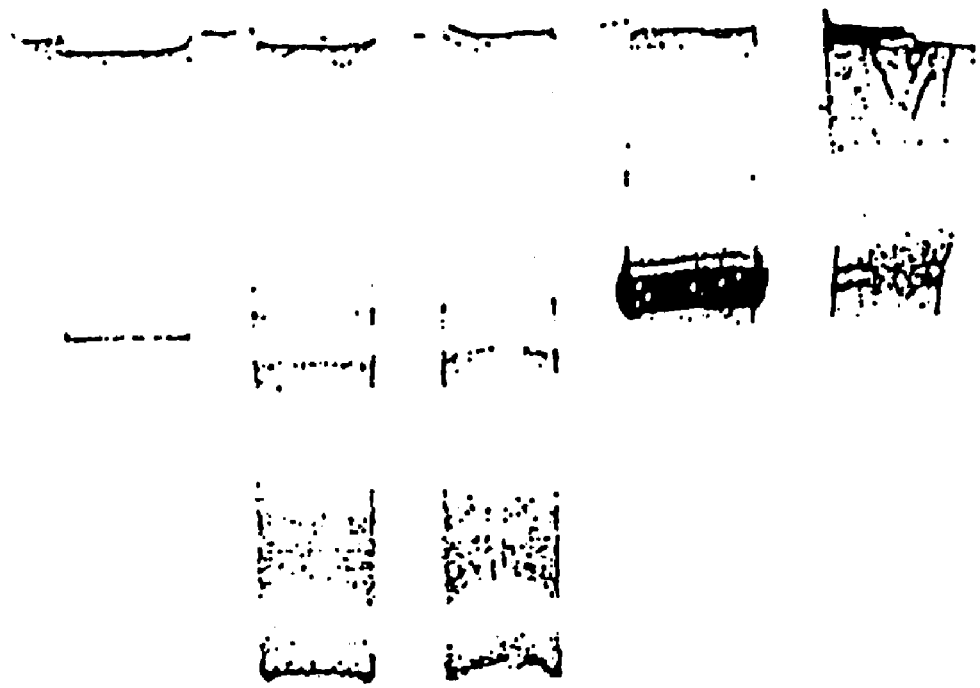
FIG. 2. SDS-polyacrylamide gel electrophoretic separations of bovine serum albumin and of fibrinogen (clottable, human). 1) Molecular weight standards (Novex See-Blue, pre-stained); 2) BSA before reaction with HRP-Px, 3) after crosslinking by HRP-Px; 4) bovine plasma fibrinogen before reaction with HRP-Px, 5) after reaction. Identical loadings of 15 µg/lane of starting material (based on samples before crosslinking and solubilization of the starting material, 10 mg/ml) was used for all samples.
Figure 2:

It was found that uncrosslinked preparations of collagens essentially were completely solubilized (>99%). Crosslinked type I collagen was found to be approximately 22–25% insoluble, type III collagen about 10% insoluble, type II collagen ~5% insoluble and type IV collagen and glutaraldehyde-crosslinked controls almost completely insoluble. Samples separated by standard SDS-polyacrylamide gel electrophoresis (SDS-PAGE) on pre-cast 7.5% gels in a tris-glycine buffer system (Bio-Rad Mini-Protean system and reagents) verified these findings (FIG. 1). Additionally, it was found that bovine fibrinogen alone was crosslinked and rendered mostly insoluble (FIG. 2), or could be co-polymerized with collagen with somewhat greater solubility but less than that of type I collagen alone (not shown). Bovine serum albumin (Sigma®) showed no effect upon reaction with HRP: Px, unlike a previous report (Stahmann et al., 1977) (FIG. 2).

It can be seen that type I and type IV collagen monomers ($\alpha$ chains) were substantially decreased after polymerization by HRP:Px, forming higher molecular weight components that barely entered the gels. Type III collagen was less affected by the polymerization reaction, while type II collagen was essentially uncrosslinked. A non-limiting hypothesis based on these observations and on SDS-agarose gel filtration profiles (following) is that the crosslinking reaction catalyzed by HRP:Px may involve lysine and hydroxylysine residues in the collagen chains, and also might involve the telopeptide regions of the collagen chains. Type II and type III collagens are prepared by limited pepsin digestion, removing the telopeptide regions and thus, potential areas of crosslinking. Type II collagen also is heavily glycosylated at its hydroxylysine residues, blocking potential reaction sites. Alternatively, type IV collagen is particularly rich in both lysine and hydroxylysine residues, and gels almost immediately upon addition of HRP:Px. Despite this, it has little mechanical strength because of its inability to form sizable fibrils. These observations support the premise of possible Schiff base condensation of lysine-hydroxylysine to form crosslinks in this system. Previous studies have suggested only dityrosine crosslinks, but apparently did not look for other possible candidates (Tenovuo and Paunio, 1979; LaBella et al, 1968).

Figure 3:
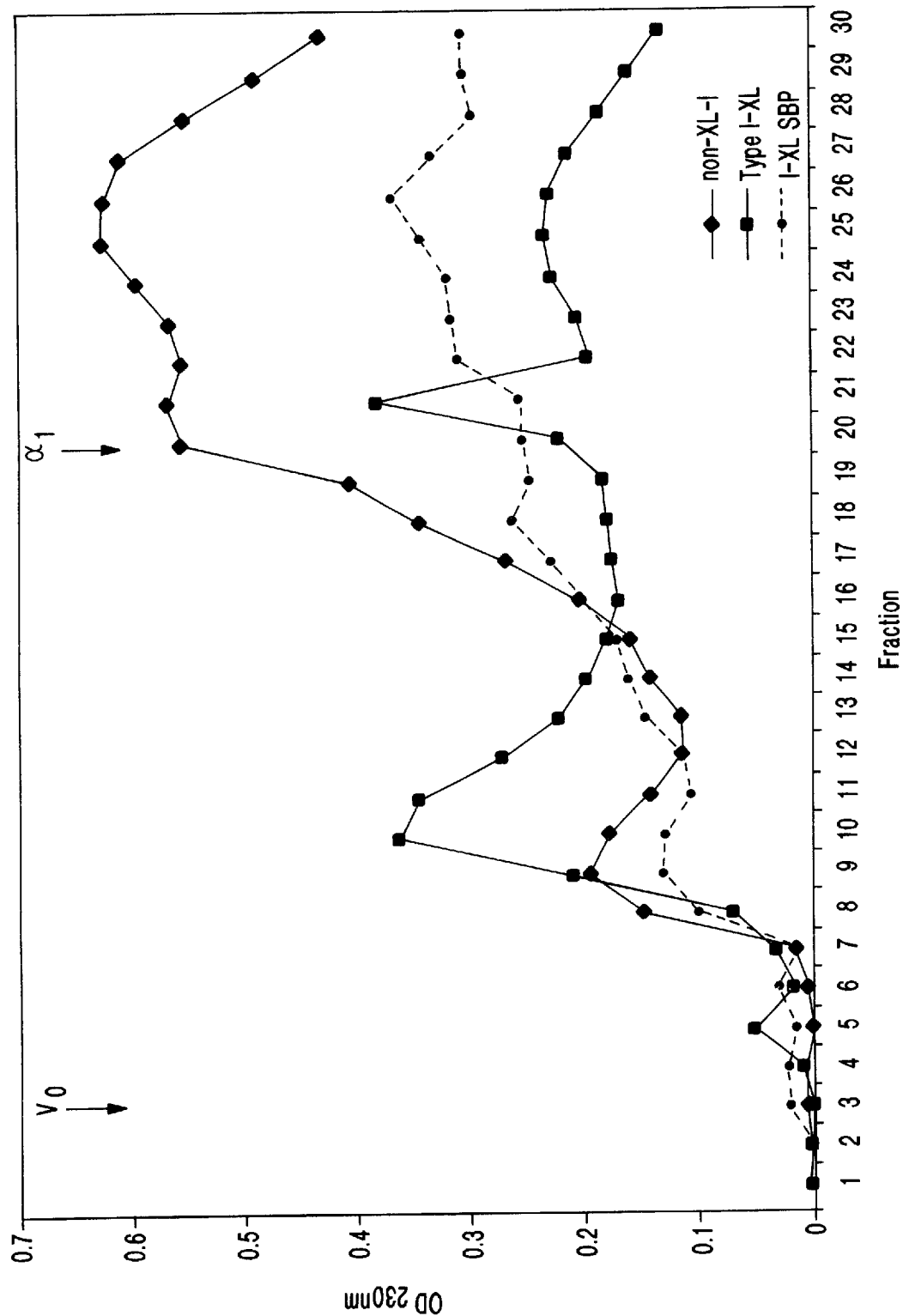
FIG. 3. Elution profiles from a Sepharose CL-6B column of SDS-solubilized type I collagen samples. Samples (10 mg/ml, 0.5 ml) were solubilized by heating in 1.0 ml of 5% SDS, 0.01 M phoshpate buffer, pH ~7.0, for 1 hour at 75° C. and the supernatants were separated on a 1×90 cm column of Sepharose. Shown are uncrosslinked (non-XL, I), HRP:Px crosslinked (Type I, XL) and Soybean Peroxidase:Px (I, XL, SBP) crosslinked sample elution profiles.
Figure 4:
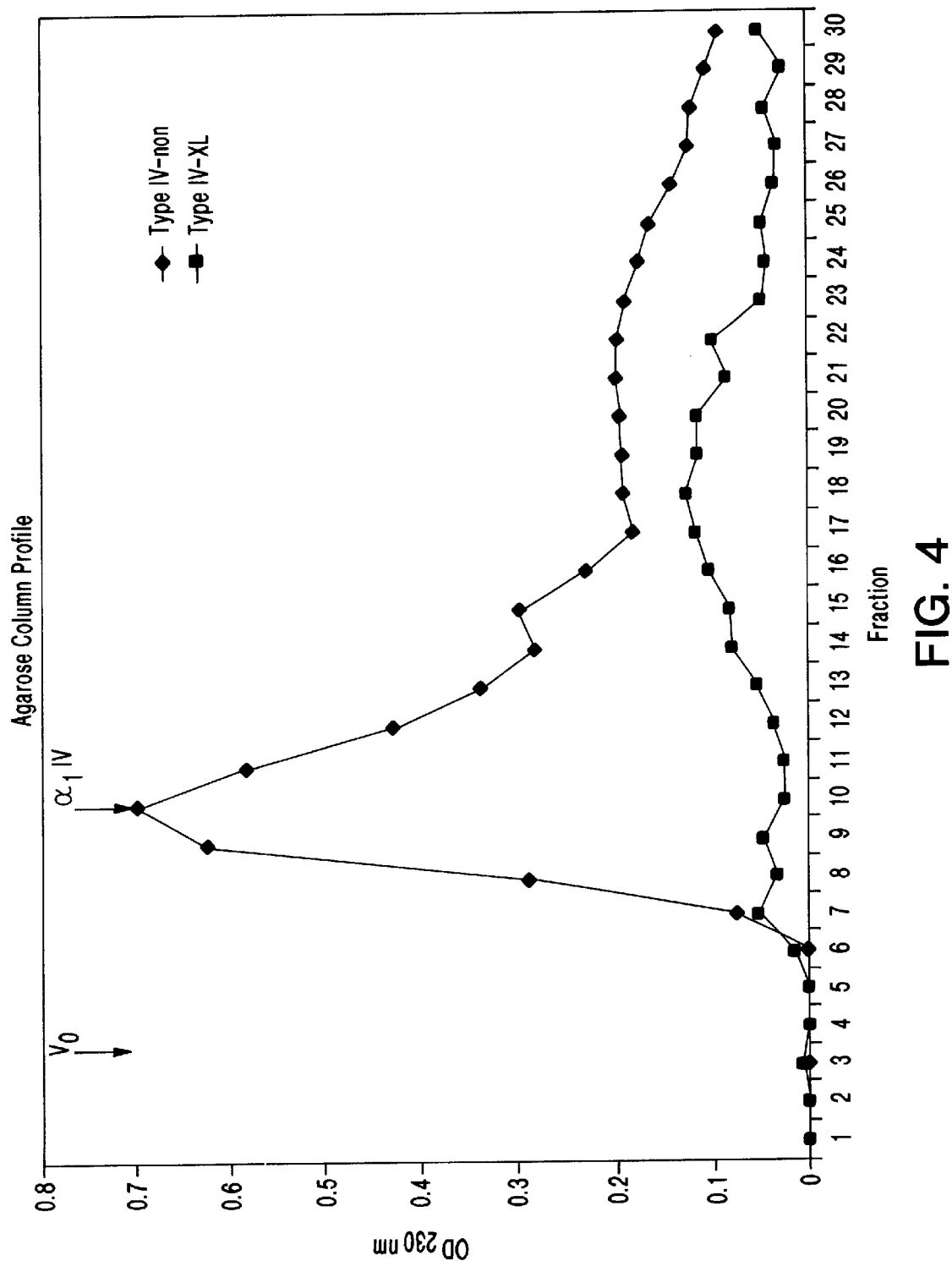
FIG. 4. Sepharose elution profiles of SDS-solubilized samples of uncrosslinked (Type IV, non) and HRP:Px crosslinked (Type IV, XL) type IV collagen done as described in FIG. 3.
Figure 5:
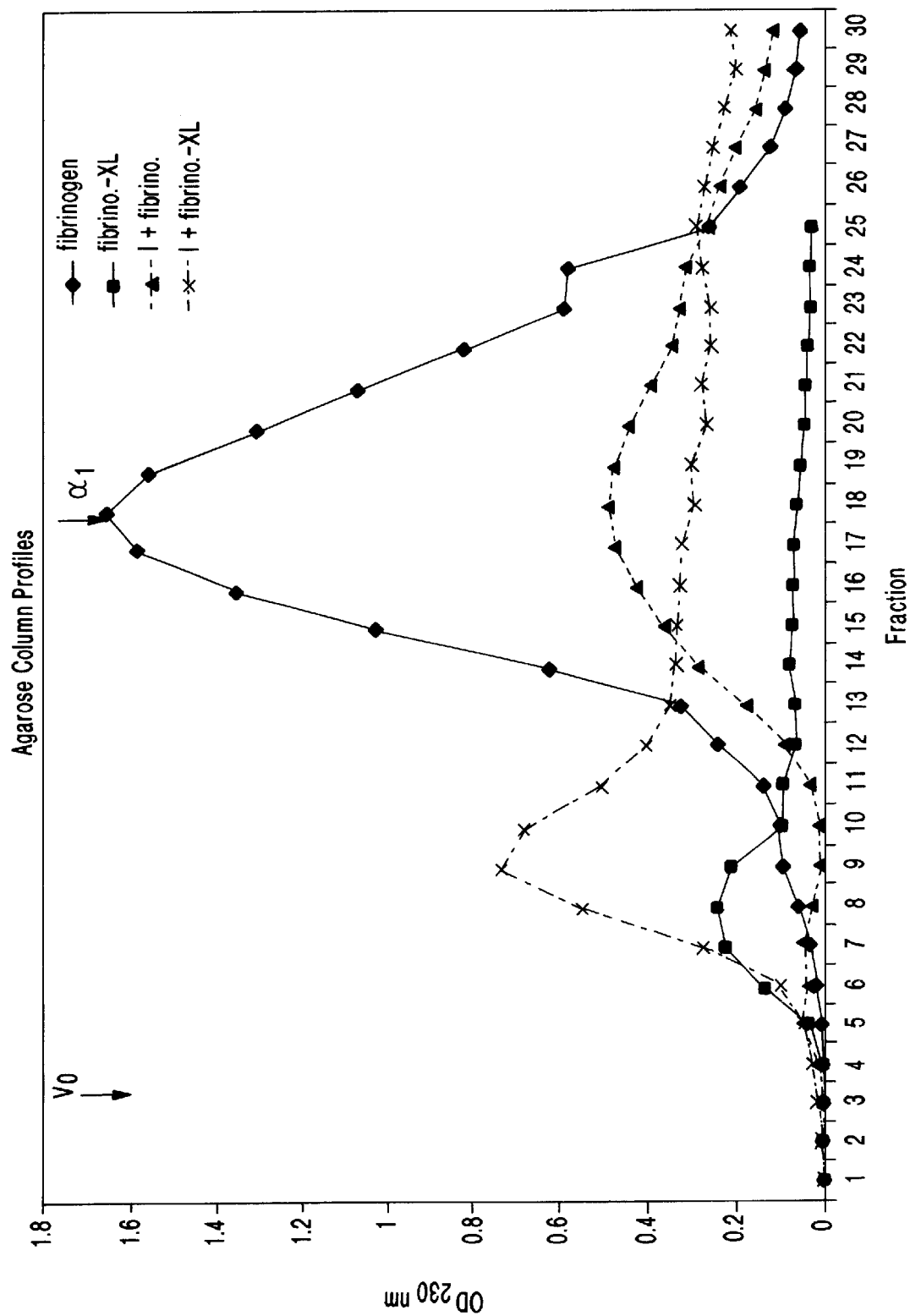
FIG. 5. Sepharose elution profiles of SDS-solubilized samples of bovine fibrinogen alone (fibrinogen) before HRP:Px crosslinking and after crosslinking (fibrino-XL), and fibrinogen plus type I collagen (8 mg/ml collagen+2 mg/ml fibrinogen) before (I+fibrino.) and after (I+fibrino.-XL) crosslinking by HRP:Px., as described in FIG. 3.

Additional aliquots of the SDS-solubilized samples were separated on a 1×90 cm water-jacketed column of Sepharose CL-6B (Pharmcia) maintained at 30° C. using 0.1% SDS in 0.01M neutral phosphate buffer as the eluant. One milliliter fractions were assessed spectrophotometrically at 230 nm. The column was calibrated using known standards. Representative profiles are shown in FIGS. 3–5. The elution position of collagen monomer chains ($\alpha_1$) and the void volume (Vo) (23–24 ml, ~fraction 3 on the graph) are indicated for reference.

Unpolymerized type I collagen was seen to elute as a broad peak in the β-α(dimer and monomer) region, with little higher molecular weight material present from $V_o$ to fraction 30 (fraction 10 on the figures). After polymerization, increased amounts of (soluble) higher MW components were found in this region accompanied by a decrease in the monomer and dimer components. The HRP, SBP and *A. ramosus* peroxidase (not shown) all produced similar profiles. Type IV collagen exhibited an even more dramatic decrease in monomer, with little of the polymerized material even being solublized to appear in the eluate. A similar disappearance of monomer and lack of high MW polymer was observed in the profiles of glutaraldehyde-crosslinked collagen (not shown). FIG. 5 shows a dramatic loss of fibrinogen monomer after crosslinking. When mixed with type I collagen, both monomers decreased and a rather large peak of higher MW material appeared. This could indicate formation of a fibrinogen-collagen co-polymer, but further results will be needed to confirm this. Similar results were obtained when collagen was polymerized with fibronectin-like engineered protein polymer (Sigma®)(not shown).

Figure 6A:
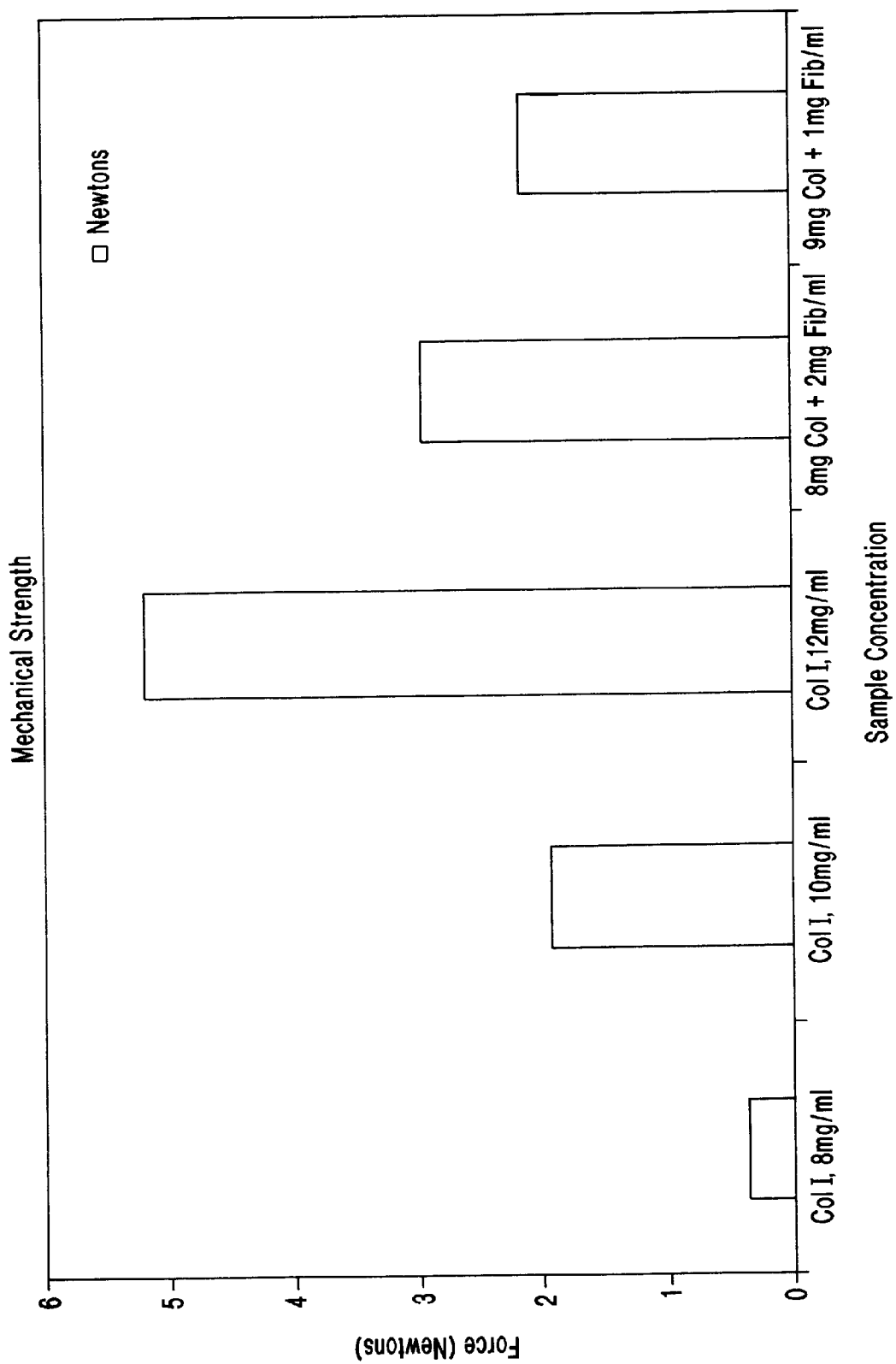
FIG. 6. Results of biomechanical testing by compression analyses in an Instron apparatus of collagen type I and collagen+bovine fibrinogen (8 mg/ml collagen+2 mg/ml fibrinogen, 9 mg/ml collagen+1 mg/ml fibrinogen) after polymerization with HRP:Px. A. Mechanical strength increased with collagen concentration and with increasing concentration of fibrinogen. B. Elasticity peaked at 10 mg/ml collagen type I and was decreased by addition of fibrinogen. Uncrosslinked collagen alone or with fibrinogen exhibited no mechanical strength or elasticity.
Figure 6B:
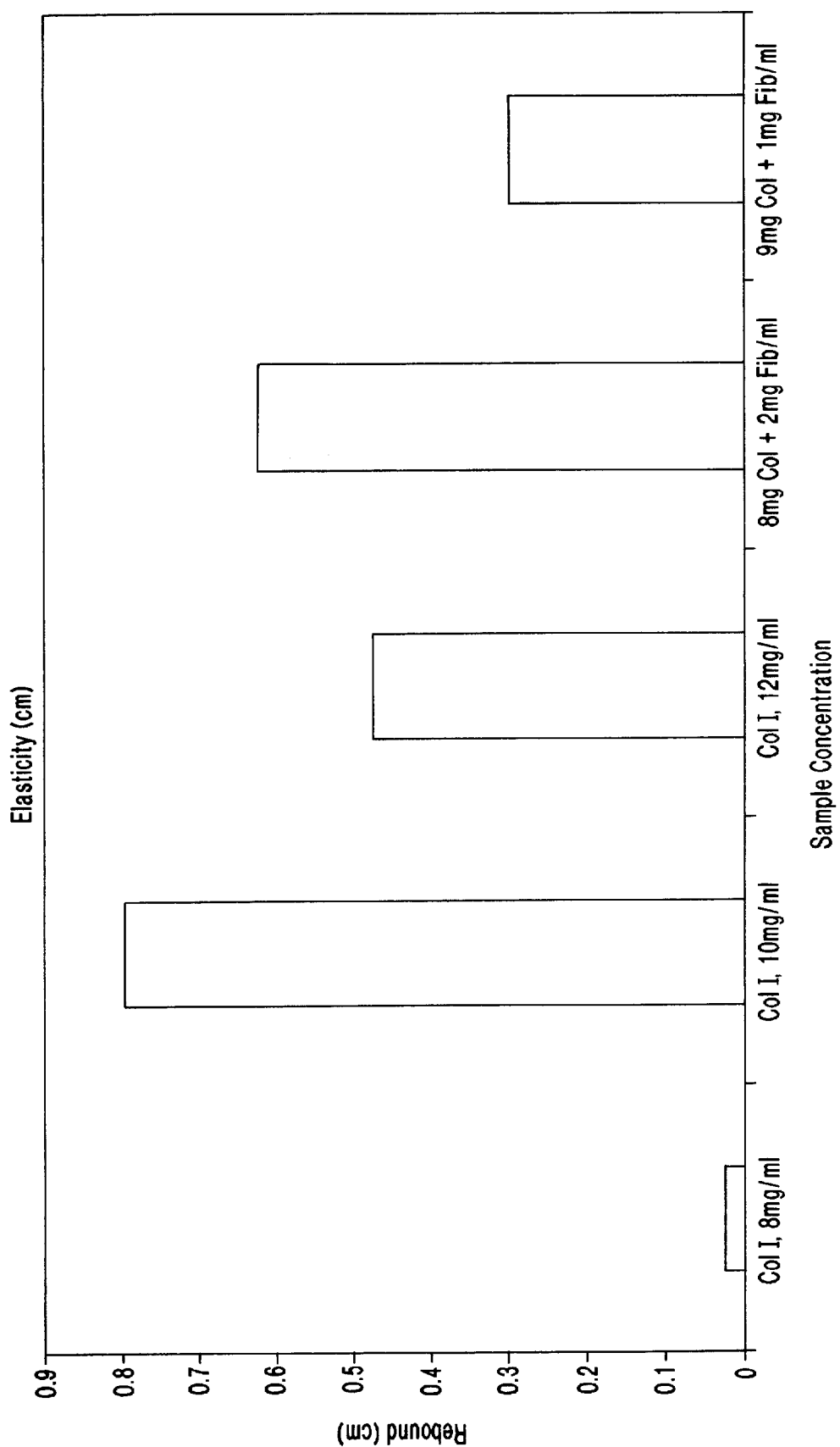

The mechanical strength and elasticity of type I collagen and type I collagen plus fibrinogen was measured by standard compression testing (Bourne, 1978) in an Instron model 1101 testing apparatus. Polymers were formed in 10×75 mm plastic tubes, removed by 'rimming,' and cut into replicate 1 cm long pieces (after trimming off both ends). The calculated mechanical strength in Newtons and elasticity (peak height in centimeters of rebound after compression) are shown in FIG. 6A and 6B. The strength of the collagen polymers increased almost linearly as the concentration increased from 8–12 mg/ml, while elasticity seemed to be at the maximum in the 10 mg/ml polymer. Adding fibrinogen to the collagen increased its mechanical strength but decreased its elasticity when compared to the same total concentration (10 mg/ml) of collagen alone.

Figure 7:
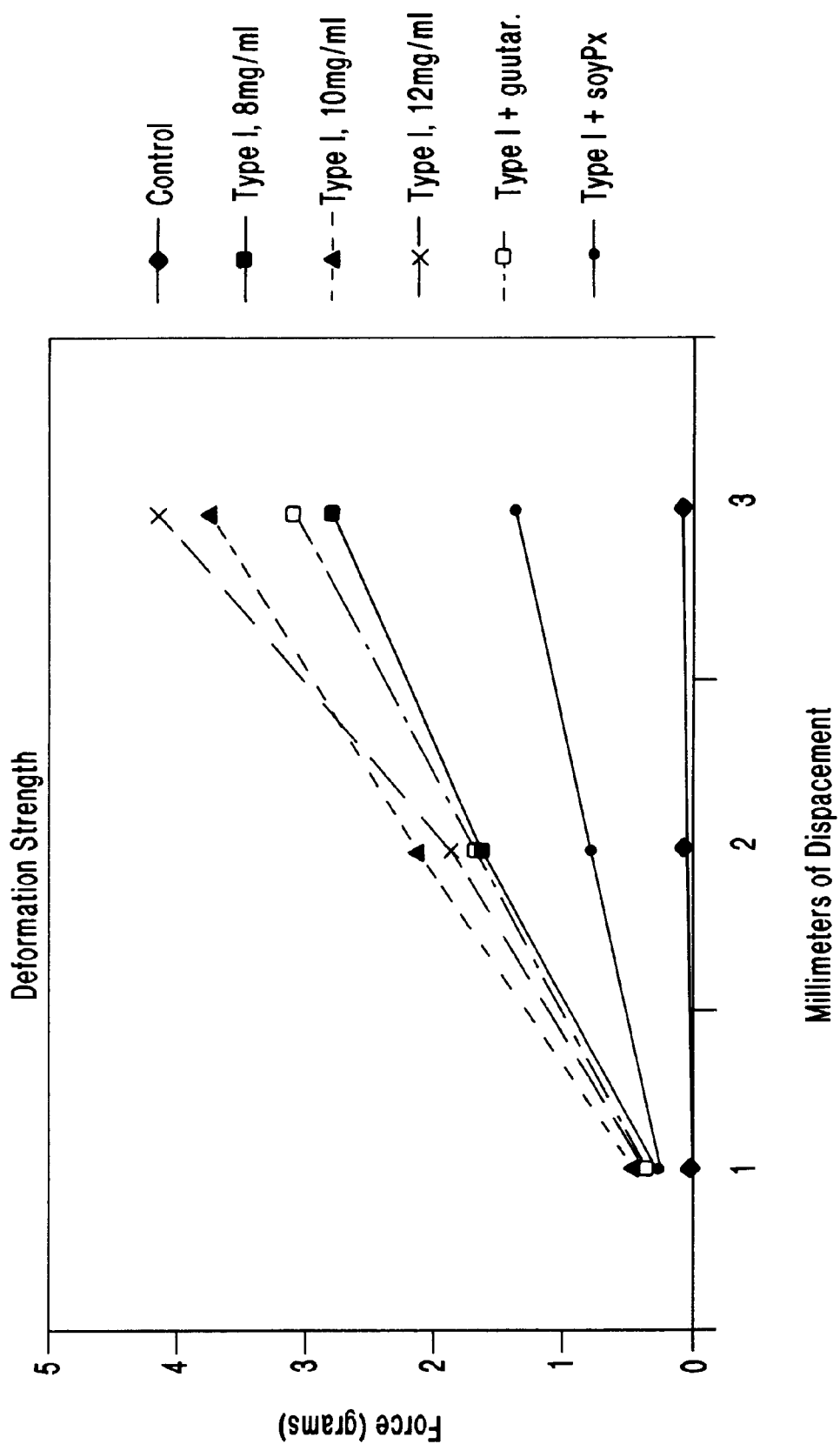
FIG. 7. Collagen type I was crosslinked at concentrations of 8, 10 and 12 mg/ml with HRP:Px (4:1:200), with 0.01% glutaraldehyde, or with soybean peroxidase (4:1:200) in individual microtiter wells (0.3 ml collagen solution/well). Samples were placed on the pan of an analytical balance and displaced by the pressure of a precision screw device producing a known displacement pressure (25% of the cross-sectional area of the samples, 0.35 mm/one turn displacement by the screw). The resulting deformation strengths of the collagen polymers are shown. It was observed that the uncrosslinked polymer (control) had no deformation resistance, while collagen polymers (containing HRP:Px) had significant strength, collagen crosslinked by glutaraldehyde had moderate strength, and collagen crosslinked by soybean peroxidase had significant strength, but less than that of HRP:Px or glutaraldhyde crosslinked collagen.

Another method of mechanical testing involved measuring the deformation resistance of collagen preparations. Type I collagen was crosslinked at concentrations of 8, 10 and 12 mg/ml with HRP:Px (4:1:200), with 0.01% glutaraldehyde, or with soybean peroxidase (4:1:200) in individual microtiter wells (0.3 ml collagen solution per 6 mm round well). Individual wells containing the samples were placed on the pan of an analytical balance and were displaced from above by the pressure of a precision screw device producing a known amount of displacement of the gel. The base of the screw contacting the gel was 25% of the cross-sectional area of the samples, and a downward displacement of 0.35 mm per turn of the screw was obtained. The resulting deformation strengths (resistance to screw pressure in grams, as measured by the balance) of the preparations is shown in FIG. 7. It was found that the uncrosslinked polymer (controls) essentially had no deformation resistance, while collagen polymers containing HRP:Px had significant strength. Collagen crosslinked by glutaraldehyde had moderate strength, while collagen crosslinked by soybean peroxidase had significant strength, but less than that of preparations crosslinked with HRP:Px or glutaraldehyde. The latter probably was due to the lesser purity of the SBP (50–150 Units/mg) versus the HRP (275–310 Units/mg).

Figure 8:
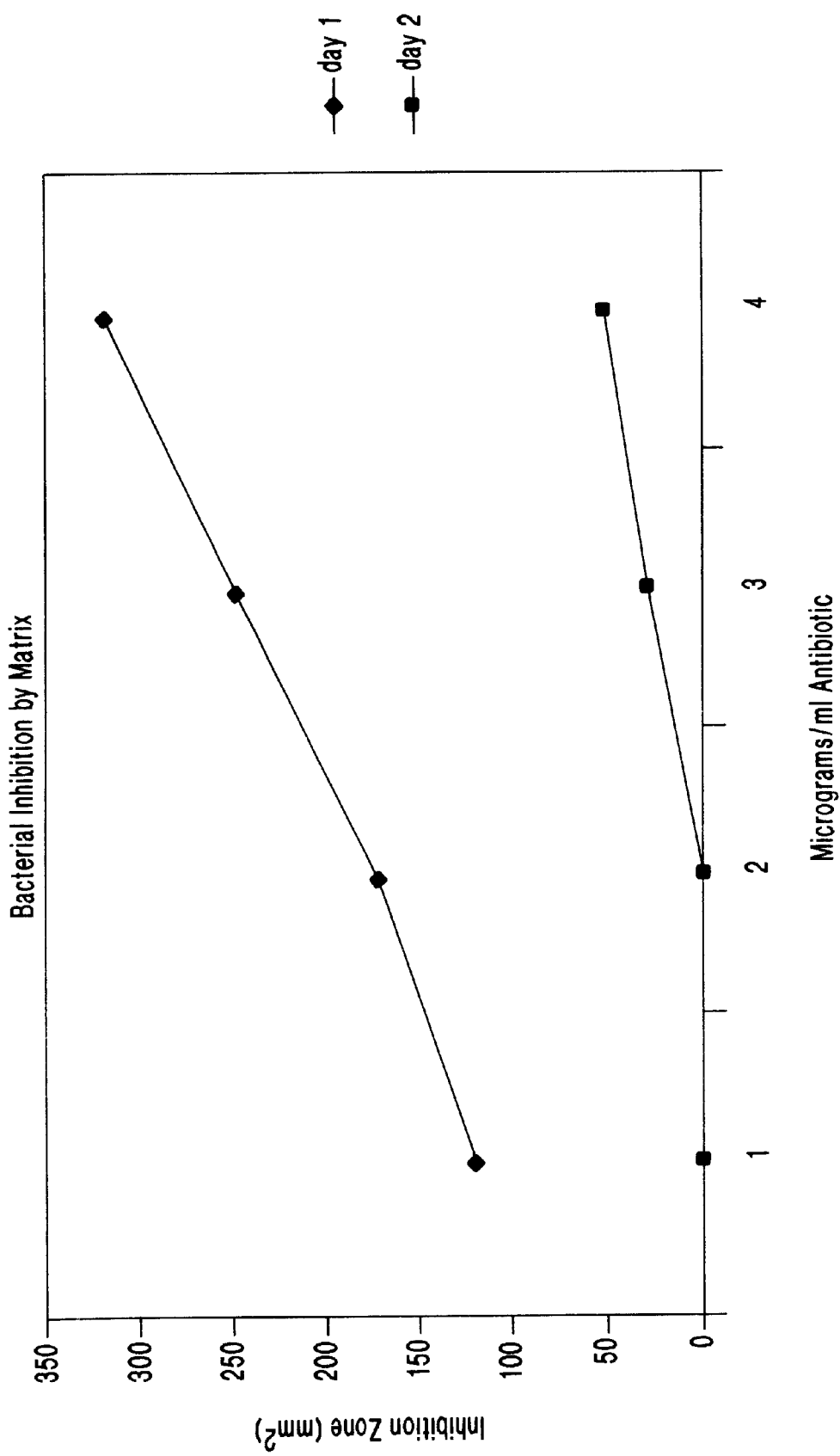
FIG. 8. Inhibition of growth of *S. aureus* in agar plates by collagen polymer matrices (plotted as area versus concentration of antibiotic). The radial area of inhibition of bacterial growth was measured, after subtracting the base area of collagen polymer plugs (6 mm diameter, 28.4 mm$^2$). Areas were measured after 1 day of exposure (day 1) followed by replacement of the plugs into a fresh culture for a second day of exposure (day 2) at the concentration of incorporated antibiotic (gentamicin) shown. The base collagen polymer (containing a final concentration of 0.006% Px) had a significant antimicribial activity on the first day (slot 1) but not on the second day.
Figure 9:
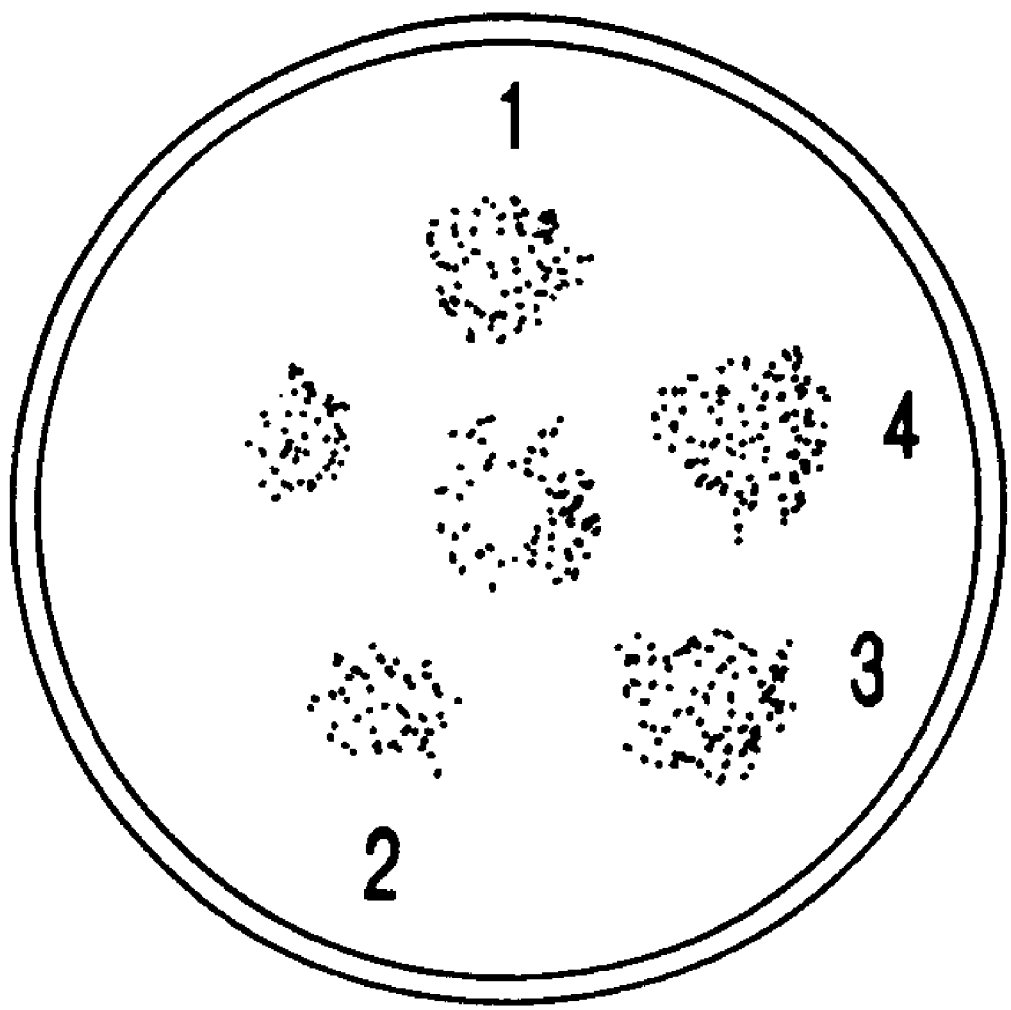
FIG. 9. Culture plate from the experiment described in FIG. 8. Number 1 is the collagen polymer alone, #2=polymer+50 μg/ml gentamicin, #3=polymer+250 μg/ml, #4=polymer+500 μg/ml. The center contains a paper disk impregnated with 250 μg/ml of gentamicin (positive control).

In additional testing, gentamicin was added to the collagen in amounts of 0–500 micrograms/ml and the polymerization was done in 96 well microtiter plates. In a modification of the Nathans agar well diffusion assay, 6 mm punches were removed from agar plates freshly seeded with *S. aureus*, and replaced with sections of the polymerized collagen. The antibiotic effectively killed the bacteria in a linear dose-responsive manner for the first 24 hours (FIGS. 8 and 9). The matrix without antibiotic also had a significant antimicrobial effect, apparently due to the peroxide. Unfortunately, the antibiotic noticeably interfered with the polymerization reaction, probably by acting as a co-reactant in the system. This problem might be overcome by incorporating the antibiotic into delayed release biodegradable microbeads thus sequestering the material from the polymerization reaction until it is complete and the excess Px has diffused away (e.g., one hour). Using dry Sephadex as a model material, it was found that the polymer beads could be added to the collagen in amounts of at least 10 weight percent relative to the collagen (1 mg Sephadex per 10 mg/ml collagen) prior to HRP catalysis without significantly affecting the integrity of the matrix after polymerization.

c. In Vitro Evaluations of Collagen Matrices with Fibroblasts

Collagen matrices (10 mg/ml) were polymerized aseptically in the bottom of triplicate 96 well culture plates (100 μl well). Fibroblasts (3T3 cells, passage 70) were freshly isolated by standard trypsinization and added to each well at approximately 33% confluency in Ham's F12 medium supplemented with 10% fetal bovine serum and antibiotics. The plates were incubated at 37° C. in a 5% $CO_2$ humidified atmosphere, and the medium was completely changed after the first day. Added to one of the plates was medium containing 2 μCi/ml each of $^3$H-thymidine and $^{14}$C-proline. The labeling was terminated after 4 hours by addition of 95% methanol followed by transfer of medium and matrices to individual scintillation vials. The matrices were dispersed by incubation with 0.5M acetic acid at 50° C. for 2 hours, precipitated by addition of ice cold trichloroacetic acid (TCA) plus 0.5% tannic acid, and filtered onto glass fiber filters with thorough washing. Radioisotopes were measured by liquid scintillation spectrophotometry and the amounts of $^3$H-thymidine (a measure of cell proliferation) and $^{14}$C-proline (a measure of protein synthesis) incorporated into precipitable counts were determined. Medium in the replicate plates was maintained and they similarly were processed on days 4 and 7 following plating.

In addition to collagen alone, it was of interest to determine if other components that might improve the bioregenerative capabilities of the matrix could be incorporated into the polymer. Therefore, fibronectin-like engineered protein polymer (Sigma®)(Fn)(0.1–1.0% of the collagen, i.e., 10–100 μg/ml) and hyaluronic acid (HA) from human umbilical cord (Sigma®)(1–5% of the collagen, i.e., 100–500 μg/ml) were added, separately or together, to the collagen immediately prior to the final addition of Px to initiate the polymerization reaction. These components had no noticeable effects on the polymerization of the matrices. The precipitable radioisotopes incorporated by cells grown on these matrices were compared to the collagen matrices alone (controls), and were expressed as a percent of their respective controls for each time period (controls=100%).

Figure 10:
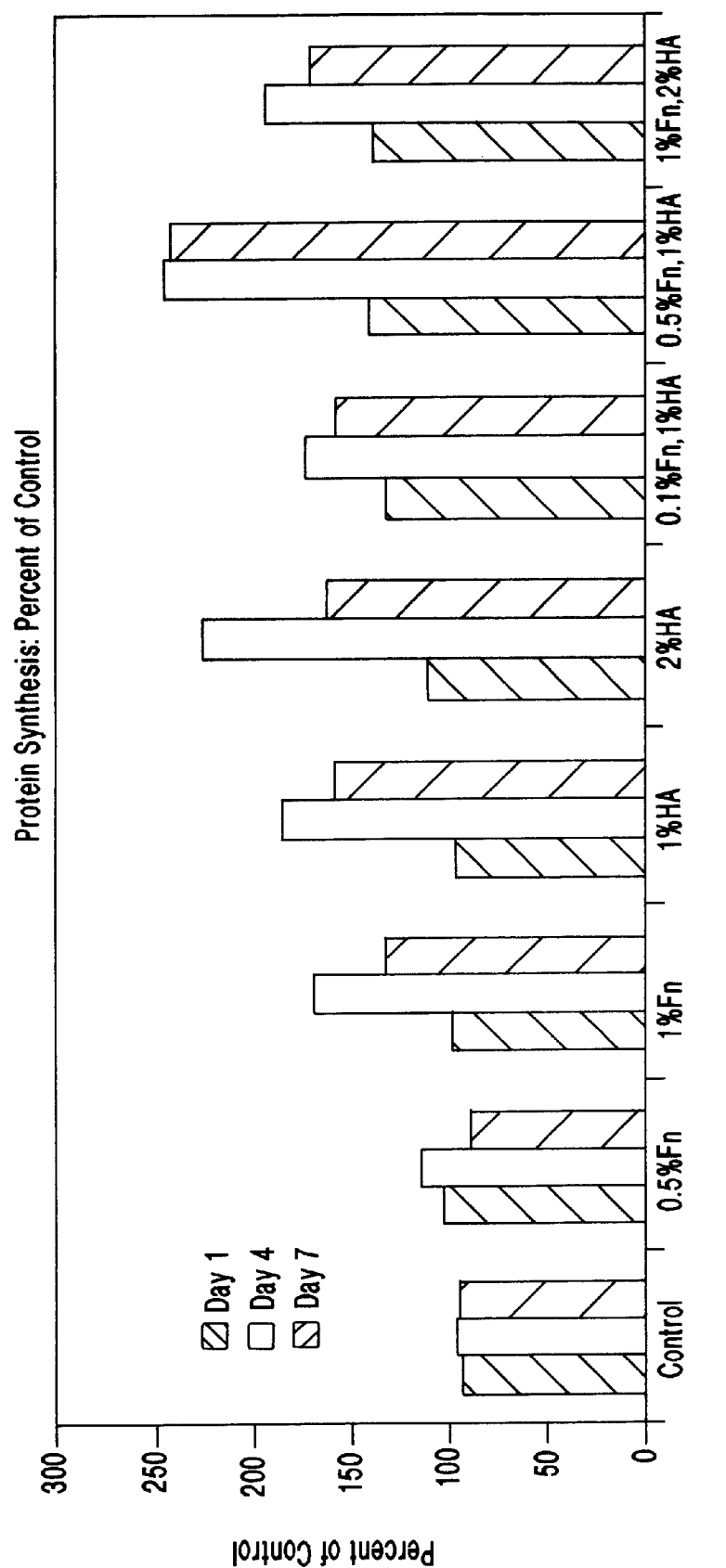
FIG. 10. Effects of matrix formulation on protein synthetic activity ($^{14}$C-proline incorporation) by 3T3 fibroblasts cultured on the collagen-based polymer matrices. Control (collagen alone, 10 mg/ml) matrix levels were taken as 100% and other preparations were expressed as a percent of the control values at the respective times indicated (1, 3, and 7 days after plating). HA=hyaluronan, Fn=fibronectin synthetic polymer, percentages are a percent of the collagen base concentration (10 mg/ml type I collagen). N=10 replicates. Student's t values (two-tailed test) for the apparent 'Best' matrix (0.5% Fn, 1% HA) versus control: P<0.07 (day 1); P<0.001 (days 4 and 7).
Figure 11:
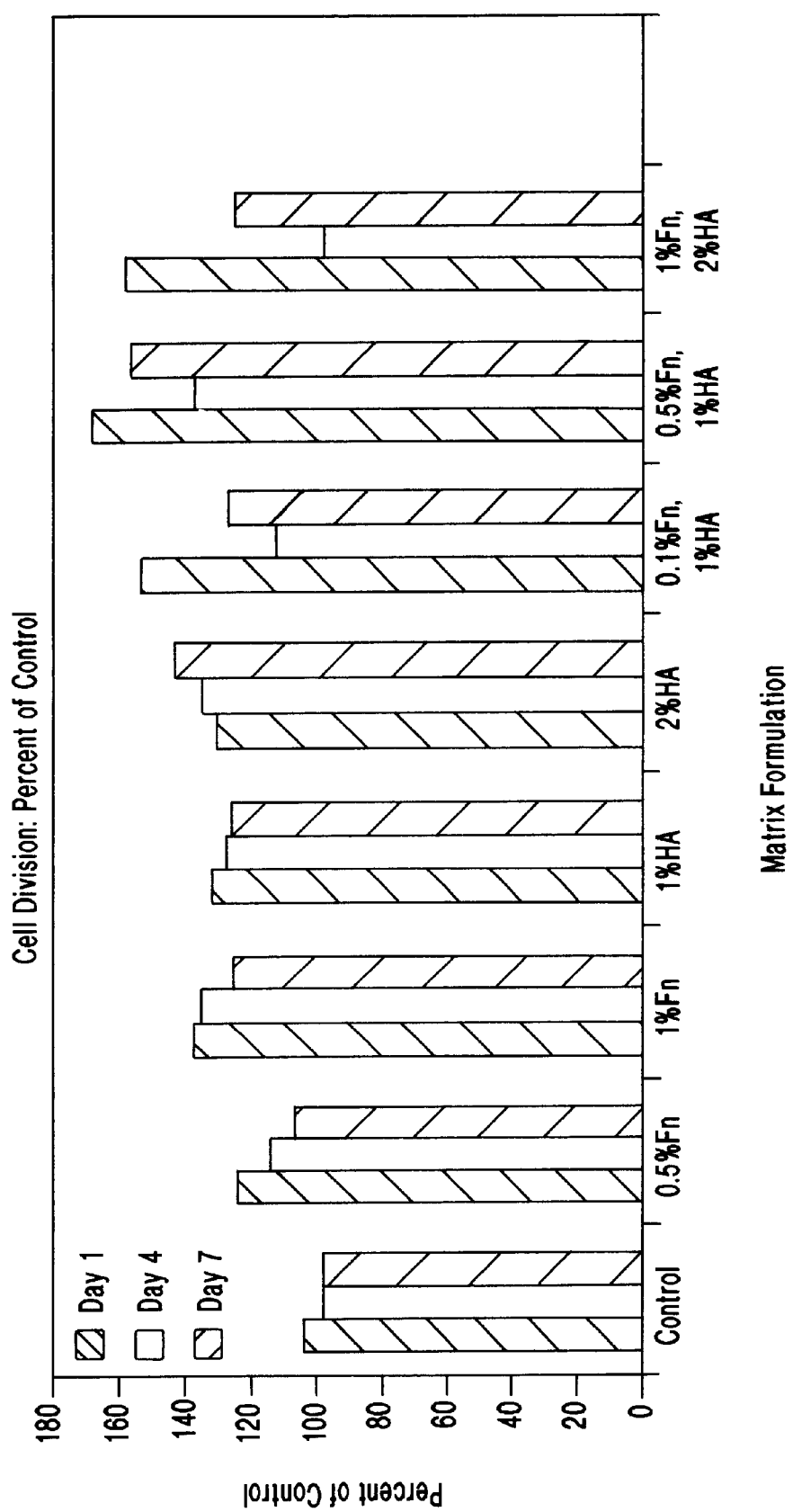
FIG. 11. Effects of matrix formulation on cellular proliferation (division) activity ($^3$H-thymidine incorporation) by 3T3 fibroblasts cultured on the collagen-based polymer matrices. Control (collagen alone, 10 mg/ml) matrix levels were taken as 100% and other preparations were expressed as a percent of the control values values at the respective times indicated (1, 3,and 7 days after plating). HA=hyaluronan, Fn=fibronectin synthetic polymer, percentages are a percent of the collagen base concentration (10 mg/ml type I collagen). N=10 replicates. Student's t values (two-tailed test) for the apparent 'Best'matrix (0.5% Fn, 1% HA) versus control: P<0.02 (day 1); P<0.001 (days 4 and 7).

Cells readily grew into the matrices, in fact, actively degrading them over the week, and exhibited no signs of cytotoxicity when examined histologically (not shown). Results for protein synthesis are shown in FIG. 10. Those for cell division (proliferation) were similar (FIG. 11). While nearly all formulations containing Fn, HA or both exhibited increased cellular activity at all time points compared to the control matrices, the most effective matrix contained 0.5% Fn+1% HA. Protein synthesis was 220–250% of controls at all three times, while cell division averaged about 150–245%. Thus, it may be concluded that the base collagen matrix can be modified by the addition of other extracellular matrix components.

Figure 12:
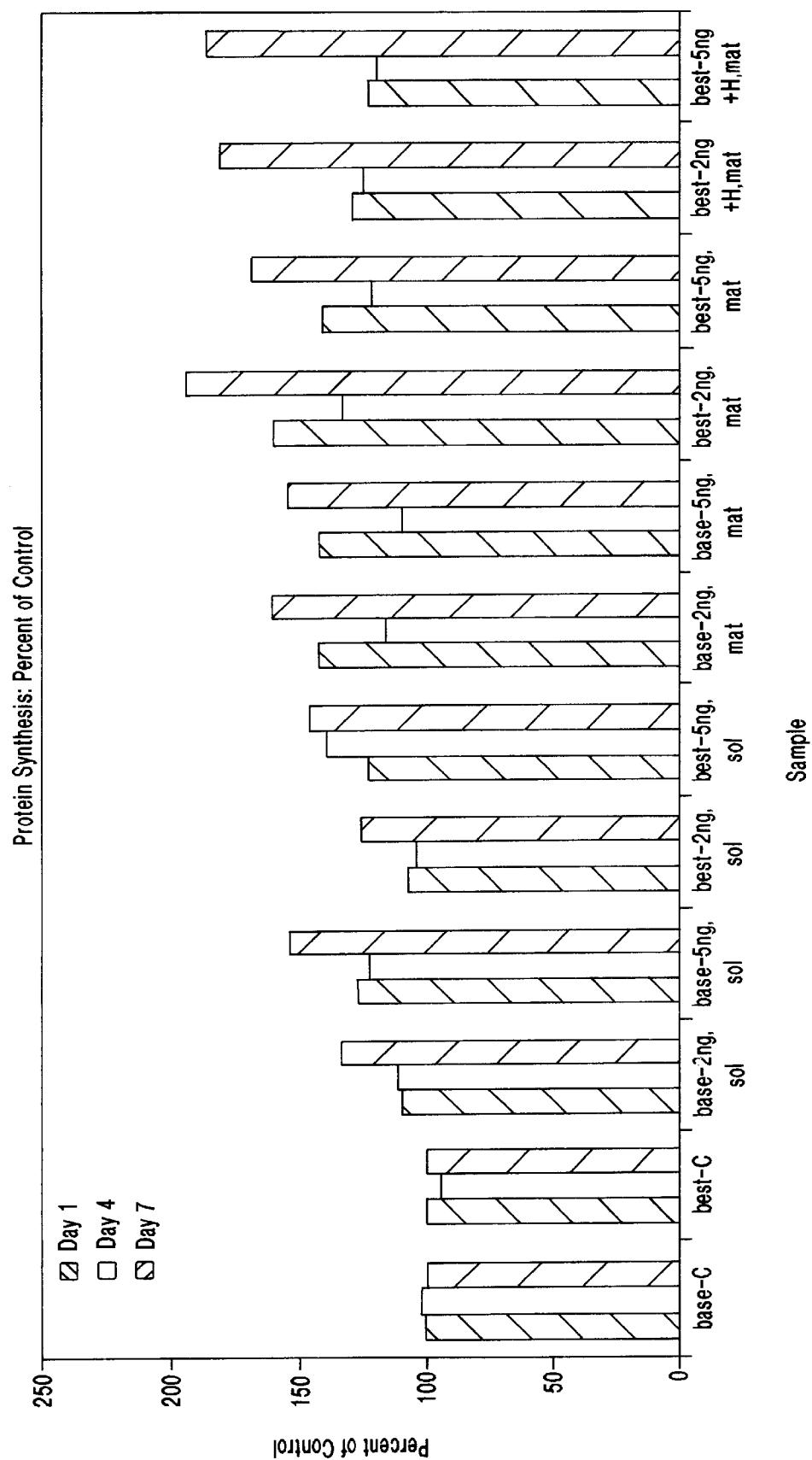
FIG. 12. Effects of recombinant human basic Fibroblast Growth Factor (rhbFGF) on protein synthetic activity ($^{14}$C-proline incorporation) by 3T3 fibroblasts cultured on the collagen-based polymer matrices. Control (collagen alone, 10 mg/ml) matrix levels (base-C) and "best" matrix (collagen, 10 mg/ml+0.5% Fn+1% HA) were taken as 100% and other preparations were expressed, respectively, as a percent of the control values at the times indicated (1, 3,and 7 days after plating). The first 2 samples represent the base and best matrix control values without added rhbFGF; the next 4 samples were incubated with 2 or 5 ng/ml rhbFGF added in solution to the culture medium (sol) to the base and best matrices; the next 4 samples with rhbFGF incorporated directly into the collagen polymer matrices (mat) as described in the text; and the final 2 preparations were the best matrix containing rhbFGF which first was combined with an equimolar amount of heparin (H) before incorporation into the collagen polymer matrix. This made no significant difference. In all of the (mat) preparations, the bFGF was added only once, while cultures receiving it in solution received fresh rhbFGF at each medium change/addition (i.e., for every 1 ng added once in the polymer, a total of 4.25 ng was added over the course of a week to culture aliquots). N=10 replicates. Student's t values (two-tailed test) for the most significant comparisons of experimental preparations versus respective controls were: Day 1: Base+2 ng, sol, NS; Base+2 ng, mat, P<0.05; Base+5 ng, sol, P<0.025; Base+5 ng, mat, P<0.01. Best+2 ng, sol, NS; Best+2 ng, mat, P<0.01; Best+5 ng, sol, NS; Best+5 ng, mat, P<0.05.

Similarly, the effects of recombinant human bFGF were investigated in culture. The base (10 mg/ml collagen alone)

and the best (collagen+0.5% Fn+1% HA) matrices were seeded with cells exposed to: 1) no bFGF; 2) either 2 or 5 ng bFGF/ml added to the culture medium; 3) 2 or 5 ng/ml added to the base and best matrices immediately prior to polymerization, and; 4) 2 or 5 ng/ml pre-mixed with an equimolar amount of heparin before addition to the best matrix Results for protein synthesis are shown in FIG. 12. Those for cell division were similar (FIG. 13). bFGF appeared to stimulate both protein synthesis and cell proliferation in both the base and best matrices on days 1 and 7, especially when it was incorporated into the best matrix with or without heparin. These results suggest that growth factors may be incorporated into the polymer matrices and retain biological activity.

In additional experiments to determine if type I collagen could be modified directly by the addition of other components, we attempted to covalently bond phosphate-containing amino acids (phosphoserine, phosphoarginine) (Sigmas®) to the collagen. To avoid direct crosslinking of the collagen, a dilute solution of type I collagen (0.2 mg/ml) was prepared in 0.01M HCl. Added to this was 5 ml PBS containing a 1500:1 molar ratio of p-serine or p-arginine to type I collagen and 1 mg of HRP+100 molar parts (relative to collagen) of peroxide. The mixtures were reacted for 6 hours at room temperature, dialyzed at 4° C. against a 1000-fold excess of 0.1 M HCl (changed twice), and lyophilized. The preparations were dissolved in standard SDS sample buffer and electrophoretically separated as described above on 7.5% polyacrylamide gels (Bio-Rad). The results (FIG. 14) show a slight increase in the apparent molecular weights of the $\alpha_1$ and $\alpha_2$ collagen chains on the gels, as compared to the untreated type I collagen standard by densitometric measurement on a Bio-Rad Fluor-S system, corresponding to an apparent binding of 2.5–3.5 phospho-amino acid residues per collagen chain (both phospho-amino acids). These results indicate that the collagen can be modified directly by binding of additional molecules. The binding of phosphate-containing amino acids could have significance to the use of such modified collagen for bone repair/prosthesis fixation.

d. Testing of the Wound Sealant in vivo

Assessment of the immunogenicity of the collagen polymer was done in five mice. Collagen preparations were made without (unpolymerized) and with (polymerized) HRP and 0.1 ml aliquots immediately were injected subcutaneously into 2 and 3 animals, respectively. This procedure was repeated 4 times at two week intervals with the animals being carefully observed each day for signs of swelling and inflammation at the injection site or any general distress or apparent discomfort. The animals were euthanized by $CO_2$ asphyxiation 4 days after the last dose and the injection sites and internal organs grossly observed. Standard H&E histology was done on the injection sites. No gross pathological changes or inflammation was found (FIG. 15), the latter being confirmed by histology.

Finally, five 6 month old rats scheduled for termination were anesthetized with Metaphane inhalent and wounds of 28.2 $mm^2$ (6 mm round) were created on opposite sides of the hindquarters by punch biopsy. HRP: Px polymerization of a 10 mg/ml collagen solution was initiated (aseptically) and immediately used to fill the wound bed on one side. The contralateral side was filled with collagen solution lacking HRP (control). The rats were individually caged and the size and appearance of the wounds monitored for 10 days. Results are shown in FIGS. 16 and 17. The collagen polymer was firmly bound to the wound beds after 5–10 minutes and remained in place for the duration. The animals at no time evidenced any discomfort or inflammation in either treated or control wounds. Wounds treated with polymer exhibited a decrease in size after just one day, while control wounds showed an average 10–15% expansion. The treated wounds retained a 1–2 day advantage of closure over controls throughout the experiment.

A similar experiment was done on eight 1 year old rats essentially as described above. In these animals, a template was used to place four wounds on the thoracic area of the back. Two punch biopsy wounds were made on each side, 1.5 cm on either side of the backbone starting at shoulder blade level and 2 cm apart anterior-posterior. In four rats, one pair of wounds served as untreated controls and the contralateral pair were filled with collagen polymer (10 mg/ml) containing in addition 0.5% Fn+1.0% HA (best matrix). The other four rats received the best matrix on one side and the best matrix plus 8 ng/ml rhbFGF on the other side. Results are shown in FIG. 18. The patterns of healing were similar to those shown above, with the best matrix exhibiting a statistically significantly greater closure over a seven day period than the controls. The best matrix+bFGF produced even more significant results, at some points being statistically superior to the best matrix alone.

e. Use of Collagen Polymer as a Binding Agent for Meat and Poultry

The solutions used for the preparation of collagen polymer were made as described above. Meat samples were prepared from approximately 20 pound samples of beef Semimembranosus muscle, trimmed free of visible fat and connective tissue. Muscle tissue was sliced into two inch cubes and minced in a bowl chopper for 20 seconds to maximize the surface area for potential binding by the collagen polymer. Aliquots of the meat (250 g) were vacuum packaged and stored at −20° C. until needed. The frozen aliquots were thawed for 12 hours at 4° C. prior to use in an experiment.

To prepare bound meat samples, 12 g portions of the above chopped meat preparations were mixed with a total of 3 ml (3 g) of collagen solution components including 1.5 ml of collagen stock solution (20 mg/ml), 0.852 ml of 0.01 M HCl, 0.528 ml of 0.2 M phosphate buffer, 60 $\mu$l of 0.3% peroxide and 60 $\mu$l of HRP (containing ~0.33 mg HRP). All materials were held at 4° C. in an ice bath. The collagen, HCl and peroxidase were combined by vortexing in a test tube and then blended into the 12 g meat aliquot by mixing the materials with a stainless steel spatula in a glass beaker for 30 seconds. The phosphate buffer and Px then were combined in a test tube, pipetting into the meat/collagen preparations, and mixed by stirring for another 30 seconds. The meat/collagen blend then was placed into a modified 60 cc syringe and extruded into 5 ml (12×75 mm) polypropylene test tubes, which then were capped and allowed to polymerize overnight at 4° C. This system produced a final formulation of 0.2% (30 mg) total added collagen per 12 g meat.

After polymerization, tubes containing the meat samples were heated to 71° C. instantaneous endpoint temperature in a circulating water bath, followed by cooling in an ice bath to 20° C. Endpoint temperatures were monitored with an Omega type K thermocouple (calibrated to the nearest 0.1° C.) placed in the geometric center of the samples.

Samples were examined by Instron compression testing, as described above, for hardness (mechanical strength) and springiness (elasticity). In experiments comparing collagen-:HRP:Px ratios on meat binding, a ratio of 4:1:50 produced meat gels that were significantly harder than those containing higher or lower levels of Px, as well as negative controls (Table 1). The meat/collagen gels showed no significant differences with differences in pH of the final product, with the treatment groups averaging a final pH of 5.71 (data not shown).

Sodium tripolyphosphate (STPP) and NaCl, common ingredients added to restructured meat products, were added to the collagen polymer system previously described to examine their individual and combined effects on the hardness and springiness of the collagen binding system. The ratio of collagen:HRP:Px in samples of the collagen polymer alone were maintained at 4:1:50, 10 mg/ml collagen concentration. NaCl was added to a final concentration of 1% (w/w), while STPP was added to a final concentration of 0.5%. Results are shown in Tables 2 and 3. No significant differences in either hardness or springiness were found in the polymer alone versus the polymer plus 1% NaCl. The addition of 0.5% STPP alone or in combination with 1% NaCl produced an approximately tenfold increase in hardness values, while springiness may have been slightly increased in some experiments where both salts were added.

In meat products restructured by addition of the collagen polymer, it was anticipated that addition of 1% NaCl, 0.5% STPP, or both would have effects similar to those observed in the collagen polymer gels (4:1:50, 10 mg/ml) alone. Results of collagen mixture+meat (20%:80%) are shown in Table 4. It was found that neither NaCl nor STPP alone significantly changed the hardness values of the meat products, while the two together resulted in a significant increase. None of the additives had any significant effect on the values for springiness.

Addition of the collagen mixture (20 wt. %, ratio of 4:1:50, 10 mg/ml collagen) to different meat and poultry sources was investigated. Bovine Semimembranosus or avian (broiler, spent hen, duck or goose) Pectoralis major were used as the meat portion of the meat/collagen polymer system. In the muscles used, beef, duck and goose had a predominance of red muscle fiber types while broiler and spent hens had predominantly white fiber types. After cooking to 71° C., samples were prepared and measured by Instron testing essentially as described above.

Results are shown in Table 5. In samples prepared from the three red meat specimens (beef, duck and goose), meat gels crosslinked with the collagen polymer were significantly harder than their respective negative controls. Springiness values were essentially unaffected. However, the white fiber poultry specimens exhibited no significant change in either parameter. Thus, this system may not be suitable for use with products containing a predominance of white muscle fibers.

It may be concluded that the hardness values achieved can be adjusted by the relative amount of collagen polymer:meat used, as well as by the addition of NaCl, STPP or both in combination. The optimal amounts of addition for each component were not precisely determined in these systems, but reasonably may be expected to vary according to the type and quality of the meat/poultry being used, and the type and final characteristics of the end product desired. That is to say, the properties of the desired product can be modified appropriately by changing the amounts of collagen mixture and salts added to the meat/poultry.

TABLE 1

Texture profile analysis of hardness and springiness values for cooked, chopped meat and added collagen polymer mixture (80% meat + 20% collagen mixture).

| $C:P:H_2O_2$ | 4:1:12.5 | 4:1:50 | 4:1:200 | Negative Control 4:0:50 |
|---|---|---|---|---|
| Hardness $(N/g)^2$ | $10.33^b$ | $11.04^a$ | $10.30^b$ | $10.03^b$ |
| SEM | .24 | .25 | .24 | .25 |
| Springiness | 2.05 | 2.04 | 2.03 | 1.96 |
| SEM | .05 | .05 | .05 | .05 |

Collagen:HRP:$H_2O_2$ was in ratios of 4:1:12.5, 50, or 200 and samples were heated to 71° C.[1]. Negative controls contained no added HRP (unpolymerized collagen mixture).
[a–b]Values within rows without common superscripts differ significantly (P < 0.05).
[1]n = 2.24 observations per treatment.
[2]N/g = Newtons/gram

TABLE 2

Texture profile analysis of hardness and springiness values for collagen polymer gels with and without added salt and/or alkaline polyphosphate.

| Collagen Formulation | Polymer[2] | Polymer w/1% NaCl | Polymer w/1% NaCl & 0.5% STPP |
|---|---|---|---|
| Hardness (N)[3] | $.41^b$ | $.40^b$ | $4.29^a$ |
| SEM | 0.17 | 0.2 | 0.17 |
| Springiness (cm) | $.80^b$ | $.57^b$ | $1.19^a$ |
| SEM | 0.09 | 0.09 | 0.08 |

[a–b]Values within rows without common superscripts differ significantly (P < 0.05).
[1]n = 4.12 observations per treatment.
[2]Extracted calf hide collagen cross-linked with C:P:$H_2O_2$ ratios of 4:1:50. 10 mg/ml collagen.
[3]N = Newtons.

TABLE 3

Texture profile analysis of hardness and springiness values for collagen polymer gels with and without added alkaline phosphate and/or salt (NaCl).

| Collagen Formulation | Polymer[2] w/ 0.5% STPP | Polymer w/0.5% STPP & 1% NaCl |
|---|---|---|
| Hardness (N)[2] [3] | 4.51 | 4.39 |
| SEM | 0.45 | 0.45 |
| Springiness (cm) | 1.65 | 1.65 |
| SEM | 0.02 | 0.02 |

Values within rows without common superscripts differ significantly (P < 0.05).
[1]n = 2.6 observations per treatment.
[2]Extracted calf hide collagen cross-linked with C:P:$H_2O_2$ ratios of 4:1:50. 10 mg/ml collagen.
[3]N = Newtons.

TABLE 4

Texture profile analysis of hardness and springiness values for cooked, chopped meat and added collagen polymer mixture (80% meat + 20% collagen mixture), with and without added salt (NaCl) and/or alkaline polyphosphate.

| Ingredients | Extract[2] | Extract w/ 1% NaCl | Extract w/ .5% STPP | Extract w/ 1% NaCl & .5% STPP | Negative Control 4:0:50 |
|---|---|---|---|---|---|
| Hardness $(N/g)^3$ | $8.79^b$ | $9.17^b$ | $8.92^b$ | $11.10^a$ | $8.00^c$ |

TABLE 4-continued

Texture profile analysis of hardness and springiness values for cooked, chopped meat and added collagen polymer mixture (80% meat + 20% collagen mixture), with and without added salt (NaCl) and/or alkaline polyphosphate.

| Ingredients | Extract[2] | Extract w/ 1% NaCl | Extract w/ .5% STPP | Extract w/ 1% NaCl & .5% STPP | Negative Control 4:0:50 |
|---|---|---|---|---|---|
| SEM | .22 | .22 | .22 | .22 | .22 |
| Springiness (cm) | 2.72 | 2.72 | 2.01 | 2.13 | 2.00 |
| SEM | .48 | .47 | .47 | .47 | .47 |

Negative controls contained no added HRP (unpolymerized collagen mixture).
Values within rows without common superscripts differ significantly (P < 0.05).
[1]n = 2.24 observations per treatment.
[2]Extracted calf hide collagen cross-linked with C:P:$H_2O_2$ ratios of 4:1:50.
Samples were 80% meat + 20% collagen mixture by weight.
[3]N/g = Newtons/gram Meade, K. R., and Silver, F. H., "Immunogenicity of collagenous implants," *Biomater.*, 11:176–180, 1990.

Pachence, J. M., Collagen-based devices for soft tissue repair," *J. Biomed. Mat. Res.*, 33:35–40, 1996.

Rault, I., Frei, V., Herbage, D., Abdul-Malak, I, and Huc, A., "Evaluation of different chemical methods for cross-linking gollagen gel, films and sponges," *J. Mat. Sci. Mat Med.*, 7:215–221, 1996.

Sierra, D. H., "Fibrin sealant adhesive systems: a review of their chemistry, material properties and clinical applications," *J. Biomat. Appl.*, 7:309–352, 1993.

Stahmann, M. A., Spencer, A. K., and Honold, G. R., "Crosslinking of proteins in vitro by peroxidase," *Biopolymers*, 16:1307–1318, 1977.

Tenovuo, J., and Paunio, K., "Peroxidase-catalysed formation of dityrosine, a protein cross-link in human periodontal ligament collagen," *Arch. Oral Biol.*, 24:591–594, 1979.

One skilled in the art readily appreciates that the present invention is well adapted to carry out the objectives and

TABLE 5

Texture profile analysis of hardness and springiness values for cooked, chopped meat and poultry from different sources (red muscle fibers and white muscle fibers) and added collagen polymer mixture (80% meat + 20% collagen mixture) with salt (NaCl) and alkaline polyphosphate.

| Meat Source | Beef[x] | Beef Negative Control[x] | Duck[x] | Duck Negative Control[x] | Goose[x] | Goose Negative Control[x] | Broiler[y] | Broiler Negative Control[y] | Spent Hen[y] | Spent Hen Negative Control[y] |
|---|---|---|---|---|---|---|---|---|---|---|
| Hardness (N/g)[2] | 12.04[a] | 10.95[b] | 8.95[a] | 7.87[b] | 7.3[a] | 6.73[b] | 10.16 | 10.50 | 9.23 | 9.85 |
| SEM | .37 | .37 | .23 | .23 | .25 | .27 | .34 | .32 | .50 | .47 |
| Springiness (cm) | 1.98 | 2.18 | 1.89 | 1.85 | 1.88 | 1.81 | 1.88 | 1.97 | 1.76 | 1.79 |
| SEM | .08 | .08 | .04 | .04 | .03 | .03 | .05 | .05 | .06 | .05 |

Negative controls contained no added HRP (unpolymerized collagen mixture)
[a–b]Comparisons within species, i.e. beef, duck, etc, in the same row without a common superscript differ significantly (P < 0.05).
[1]n = 2, 24 observations per treatment, collagen mixture added at 20%.
[2]N/g = Newtons/gram.
[x]Red fiber type predominant; beef = Semimembranosus, poultry = *Pectoralis major*
[y]White fiber type predominant; *Pectoralis major*

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Bourne, M. C., "Texture profile analysis," *Food Technol.*, 32:62–72, 1978.

Choucair, M., and Phillips, T., "A review of wound healing and dressing materials,"*Wounds*, 8:165–172, 1996.

Jain, M. K., "Collagen: biomaterial properties and applications in medical devices,"Product literature for BioCore, Inc., Topeka, Kans., 1992.

Jeter, K. F., and Tintle, T. E., "Wound dressings of the nineties: indications and contraindications," *Clin. Pod. Med. Surg.*, 8 :799–816, 1991.

LaBella, F., Waykole, P., and Queen, G., "Formation of insoluble gels and dityrosine by the action of peroxidase on soluble collagens," *Biochem. Biophys. Res. Comm.*, 30: 333–338, 1968.

Lasa, C. I., Kidd, R. R., Nunez, H. A., and Drohan, W. N., "Effect of fibrin glue and opsite on open wounds in db/db mice," *J. Surg. Res.*, 54:202–206, 1993.

obtain the ends and advantages mentioned as well as those inherent therein. Systems, pharmaceutical compositions, treatments, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed is:

1. A method of sealing a wound comprising the steps of:
   applying to a wound a mixture of collagen and a crosslinking agent, wherein the collagen is selected from the group consisting of Type I collagen, Type II collagen, Type III collagen and Type IV collagen and the crosslinking agent is peroxidase and hydrogen peroxide ($H_2O_2$);
   crosslinking said collagen in said wound, whereby said crosslinking forms a semi-solid gel that seals said wound.

2. The method of claim 1, wherein the crosslinking agent is selected from the group consisting of horseradish peroxidase (HRP) and hydrogen peroxide ($H_2O_2$); or soybean peroxidase and hydrogen peroxide ($H_2O_2$), or microbial peroxidase from *Arthromyces ramosus* and hydrogen peroxide ($H_2O_2$).

3. The method of claim 2, wherein the crosslinking agent is horseradish peroxidase (HRP) and hydrogen peroxide ($H_2O_2$).

4. The method of claim 3, wherein the molar ratios of collagen to horseradish peroxidase to hydrogen peroxide range from 4 to 5 collagen to 1 horseradish peroxidase to 50 hydrogen peroxide (4–5:1:50), to 4 to 5 collagen to 1 horseradish peroxidase to 200 hydrogen peroxide (4–5:1:200).

5. The method of claim 3, wherein the collagen concentration ranges from 8 mg/ml to 12 mg/ml.

6. The method of claim 4, wherein the collagen concentration ranges from 8 mg/ml to 12 mg/ml.

7. The method of claim 1, wherein the collagen is Type I collagen.

8. The method of claim 7, wherein the collagen is Type I collagen from calf skin.

9. The method of claim 1, wherein the semi-solid gel has properties consisting of decreased solubility of matrices in hot (75° C.) sodium dodecyl sulfate (SDS) solution, and an increase in high molecular weight components observed by SDS agarose gel filtration and SDS-polyacrylamide gel electrophoresis with a concomitant decrease in lower molecular weight components.

10. The method of claim 1, wherein the mixture applied to the wound further comprises at least one additional agent.

11. The method of claim 10, wherein the additional agent is a delivery agent.

12. The method of claim 10, wherein the additional agent is selected from the group consisting of proteins, vaccine antigens, adjuvants, growth factors, microbeads and drugs.

13. The method of claim 10, wherein the additional agent is selected from the group consisting of bovine serum albumin, fibrinogen, fibronectin, fibroblast growth factor, and human placental hyaluronic acid.

14. The method of claim 10, wherein the additional agent is biologically active.

15. The method of claim 14, wherein the additional agent stimulates cell growth and/or synthetic activities.

16. The method of claim 10, wherein said additional agent in said gel has biological activity.

17. The method of claim 16, wherein the additional agent is a growth factor.

18. The method of claim 17, wherein said growth factor is fibroblast growth factor.

19. The method of claim 10, wherein the additional agent is fibrinogen.

20. The method of claim 19, wherein type I collagen and fibrinogen form a copolymer.

21. The method of claim 1, wherein the gel is poorly or non-immunogenic.

22. The method of claim 10, wherein the additional agent comprises biodegradable microbeads containing an antimicrobial agent allowing for delayed release.

23. The method of claim 10, wherein the wound is in bone, and the additional agent comprises phospo-amino acids.

24. The method of claim 23, wherein the gel provides a matrix material suitable for stimulation of mineralization.

25. The method of claim 23, wherein the gel provides a matrix suitable for fixation of an orthopedic or dental implant in said bone.

26. A method of forming a semi-solid crosslinked polymer on the surface of meat or poultry tissues for use as a food binding/restructuring agent comprising the steps of crosslinking a protein with a peroxidase in the presence of peroxide, wherein the protein is selected from the group consisting of Type I collagen, Type II collagen, Type III collagen, and Type IV collagen, fibrinogen, and recombinant fibronectin engineered protein polymer, and the peroxidase is selected from the group consisting of horseradish peroxidase, soybean peroxidase, and microbial peroxidase from *Arthromyces ramosus*.

27. The method of claim 26, wherein the protein is type I collagen and the peroxidase is horseradish peroxidase.

28. A method for growing dermal fibroblasts in vitro comprising the steps of growing the fibroblasts in a peroxide crosslinked collagen polymer comprising a three dimensional matrix for the growth of said dermal fibroblasts in vitro.

29. The method of claim 28 wherein said dermal fibroblasts are mouse 3T3 cells.

30. The method of claim 28, wherein the collagen is Type I collagen and has been crosslinked with horseradish peroxidase and hydrogen peroxide.

* * * * *

UNITED STATES PATENT AND TRADEMARK OFFICE
CERTIFICATE OF CORRECTION

PATENT NO. : 6,509,031 B1
DATED : January 21, 2003
INVENTOR(S) : Douglas R. Miller et al.

It is certified that error appears in the above-identified patent and that said Letters Patent is hereby corrected as shown below:

Column 2,
Line 65, delete "($H_2O_2$, $O_2$, Px)" and insert -- ($H_2O_2$, Px) --

Column 7,
Line 45, delete "antimicribial" and insert -- antimicrobial --

Column 12,
Line 53, delete "Pharmcia" and insert -- Pharmacia --

Column 15,
Line 27, delete "0.1" and insert -- 0.01 --

Column 18,
Table 1, after "Springiness" add -- (cm) --
Table 2, in description of table, after "added salt" insert -- (NaCl) --

Column 19,
Table 4 continued, before "Values within rows..." insert as superscript -- a-c --

Signed and Sealed this

Twenty-seventh Day of May, 2003

JAMES E. ROGAN
*Director of the United States Patent and Trademark Office*